United States Patent
Reguera et al.

(10) Patent No.: US 12,378,290 B2
(45) Date of Patent: Aug. 5, 2025

(54) METHOD FOR PROTEIN NANOWIRE SYNTHESIS AND TUNABLE CONTROL OF NANOWIRE LENGTH

(71) Applicant: Board of Trustees of Michigan State University, East Lansing, MI (US)

(72) Inventors: Gemma Reguera, East Lansing, MI (US); Krista Marie Cosert, Sacramento, CA (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 18/483,343

(22) Filed: Oct. 9, 2023

(65) Prior Publication Data

US 2024/0132549 A1   Apr. 25, 2024

Related U.S. Application Data

(62) Division of application No. 16/995,163, filed on Aug. 17, 2020, now abandoned.

(60) Provisional application No. 62/896,179, filed on Sep. 5, 2019.

(51) Int. Cl.
| | |
|---|---|
| *H01B 1/12* | (2006.01) |
| *C07K 14/195* | (2006.01) |
| *B82Y 5/00* | (2011.01) |
| *B82Y 30/00* | (2011.01) |

(52) U.S. Cl.
CPC ............. *C07K 14/195* (2013.01); *H01B 1/12* (2013.01); *B82Y 5/00* (2013.01); *B82Y 30/00* (2013.01)

(58) Field of Classification Search
None
See application file for complete search history.

(56) References Cited

U.S. PATENT DOCUMENTS

| | | | |
|---|---|---|---|
| 5,418,140 A | 5/1995 | Chang et al. | |
| 5,834,247 A | 11/1998 | Comb et al. | |
| 5,968,769 A | 10/1999 | Green et al. | |
| 6,897,285 B2 | 5/2005 | Xu et al. | |
| 6,984,505 B2 | 1/2006 | Xu et al. | |
| 6,987,007 B2 | 1/2006 | Xu et al. | |
| 7,001,745 B1 | 2/2006 | Xu et al. | |
| 7,060,465 B2 | 6/2006 | Xu et al. | |
| 7,271,256 B2 | 9/2007 | Evans et al. | |
| 7,498,155 B2 | 3/2009 | Lovley et al. | |
| 7,517,671 B2 | 4/2009 | Taron et al. | |
| 7,732,565 B2 | 6/2010 | Taron et al. | |
| 8,729,233 B2 | 5/2014 | Reguera et al. | |
| 8,846,890 B2 | 9/2014 | Reguera et al. | |
| 9,409,955 B2 | 8/2016 | Reguera et al. | |
| 9,601,227 B2 | 3/2017 | Reguera et al. | |
| 9,716,287 B2 | 7/2017 | Reguera et al. | |
| 10,074,867 B2 | 9/2018 | Reguera et al. | |
| 2003/0216550 A1 | 11/2003 | Xu et al. | |
| 2005/0196804 A1 | 9/2005 | Xu et al. | |
| 2005/0196841 A1 | 9/2005 | Xu et al. | |
| 2006/0030008 A1 | 2/2006 | Xu et al. | |
| 2006/0035333 A1 | 2/2006 | Taron et al. | |
| 2006/0041849 A1 | 2/2006 | Aitnouri et al. | |
| 2006/0199225 A1 | 9/2006 | Colussi et al. | |
| 2007/0065880 A1 | 3/2007 | Taron et al. | |
| 2007/0099234 A1 | 5/2007 | Zhang et al. | |
| 2010/0167942 A1 | 7/2010 | Zheng et al. | |
| 2011/0071280 A1 | 3/2011 | Taron et al. | |
| 2011/0097737 A1 | 4/2011 | Samuelson et al. | |
| 2012/0053319 A1 | 3/2012 | Reguera et al. | |
| 2012/0053320 A1 | 3/2012 | Reguera et al. | |
| 2014/0239237 A1 | 8/2014 | Reguera et al. | |
| 2014/0336357 A1 | 11/2014 | Reguera et al. | |

FOREIGN PATENT DOCUMENTS

| | | |
|---|---|---|
| EP | 0036776 A2 | 9/1981 |
| JP | 2010033344 A | 2/2010 |
| WO | 2001057183 A2 | 8/2001 |
| WO | 2003074660 A2 | 9/2003 |
| WO | 2006041849 A2 | 4/2006 |
| WO | 2006096821 A1 | 9/2006 |
| WO | 2009026089 A1 | 2/2009 |
| WO | 2013033456 A2 | 3/2013 |
| WO | 2013033456 A3 | 3/2013 |

OTHER PUBLICATIONS

Lutz, Helmut et al, "Acetylation dictates the morphology of nanophase biosilica precipitated by a 14 amino acid leucine-lysine peptide." J. Peptide Sci. (2016) 23 p. 141-147.*
Raoufinia, Ramin et al, "Overview of albumin and its purification methods." Adv. Pharm. Bull. (2016) 6(4) p. 495-507.*
Gorbitz, Carl Henrick; "The structure of nanotubes formed by diphenyulalanine, the core recognition motif of alzheimer's beta-amyloid polypeptide." Chem. Comm. (2006) p. 2332-2334.*
Penzol, Guadalupe et al, "Use of dextrans as long and hydrophilic spacer arms to improve the performance of immobilized proteins acting on macromolecules." Biotech. Bioengin (1998) 60(4) p. 518-523.*

(Continued)

*Primary Examiner* — Fred H Reynolds
(74) *Attorney, Agent, or Firm* — Westman, Champlin & Koehler, P.A.; Amanda M. Prose

(57) ABSTRACT

Methods for synthesizing nanowires are provided. Modified PilA peptides are used as peptide building blocks for synthesizing the nanowires. The method places the peptide building blocks in an assembly buffer with a hydrophobe. Addition of a hydrophobe and molecular crowding by evaporation of the assembly buffer triggers the self-assembly of the peptide building blocks into fibers. Multiple elongation cycles of addition of peptide building blocks, mixing and evaporation are conducted to promote elongation of the fibers and synthesis of nanowires. Electronic characterization of the synthesized nanowires is provided.

5 Claims, 11 Drawing Sheets
Specification includes a Sequence Listing.

(56) References Cited

OTHER PUBLICATIONS

Whitmore et al., "Protein Secondary Structure Analyses from Circular Dichroism Spectroscopy: Methods and Reference Databases", Biopolymers, May 2008, pp. 392-400, vol. 89, No. 5.
Wootton et al., "Statistics of Local Complexity in Amino Acid Sequences and Sequence Databases", Computers and Chemistry, Jun. 1993, pp. 149-163, vol. 17, No. 2.
Yang et al., "Metabolic Response of Geobacter sulfureducens Towards Electron Donor/Acceptor Variation", Microbial Cell Factories, Nov. 2010, vol. 9, No. 90, 15 pages.
Del Medico, Luca et al. "The type IV pilin PilA couples surfactant attachment and cell cycle initiation in Caulobacter crescentus." PNAS (2020)117(17) p. 9546-9553.
Liu, Xinying et al. "Direct Observations of Electrically conductive Pili Emanating from Geobacter sulfurreducens." mBio (2021) 12e02209-21.
Sun, Hongyan et al. "Influence of particle size on the aggregation behavior of nanoparticles: Role of structural hydration layer." J. Environ. Sci. (2021) 103 p. 33-42.
Hsieh, Andrew G. et al. "Despersion stability of functionalized graphene in aqueous sodium dodecyl sulfate solutions." Langmuir (2013) 29 p. 14831-14838.
Sager, Tina M. et al. "Improved method to disperse nanoparticles for in vitro and in vivo investigation of toxicity" Nanotoxicology (2007) 1(2) p. 118-129.
Kaur, Inder et al; "Dispersion of nanomaterials in aqueous media: towards protocol optimization." J. Vis. Exp. (130) e56074, 2017.
Muller, F. et al. "Dispersing nanoparticles in liquids." Int. J. Miner. Process (2004) 74S p. S31-S41.
Sumitomo, Syunsuke et al. "Comparision of dispersion behavior of agglomerated particles in liquid between ultrasonic irradiation and mechanical stirring." Ultrasonics (2018) 40 p. 822-831.
Restriction Requirement received for U.S. Appl. No. 13/221,459, mailed on Nov. 9, 2012, 6 pages.
Non-Final Office Action received for U.S. Appl. No. 13/221,459, mailed on Jan. 8, 2013, 10 pages.
Final Office Action received for U.S. Appl. No. 13/221,459, mailed on Jun. 26, 2013, 13 pages.
Advisory Action received for U.S. Appl. No. 13/221,459, mailed on Sep. 9, 2013, 3 pages.
Notice of Allowance received for U.S. Appl. No. 13/221,459, mailed on Jan. 2, 2014, 8 pages.
Restriction Requirement received for U.S. Appl. No. 13/221,495, mailed on Mar. 13, 2013, 8 pages.
Non-Final Office Action received for U.S. Appl. No. 13/221,495, mailed on Jul. 12, 2013, 18 pages.
Final Office Action received for U.S. Appl. No. 13/221,495, mailed on Nov. 7, 2013, 21 pages.
Advisory Action received for U.S. Appl. No. 13/221,495, mailed on Jan. 27, 2014, 2 pages.
Notice of Allowance received for U.S. Appl. No. 13/221,495, mailed on May 27, 2014, 8 pages.
Restriction Requirement received for U.S. Appl. No. 14/193,943, mailed on Jan. 5, 2016, 9 pages.
Non-Final Office Action received for U.S. Appl. No. 14/193,943, mailed on Apr. 7, 2016, 13 pages.
Final Office Action received for U.S. Appl. No. 14/193,943, mailed on Aug. 12, 2016, 8 pages.
Notice of Allowance received for U.S. Appl. No. 14/193,943, mailed on Nov. 3, 2016, 8 pages.
Restriction Requirement received for U.S. Appl. No. 14/448,843, mailed on Apr. 6, 2015, 6 pages.
Non-Final Office Action received for U.S. Appl. No. 14/448,843, mailed on Jun. 24, 2015, 21 pages.
Final Office Action received for U.S. Appl. No. 14/448,843, mailed on Oct. 22, 2015, 6 pages.
Advisory Action received for U.S. Appl. No. 14/448,843, mailed on Jan. 8, 2016, 4 pages.
Notice of Allowance received for U.S. Appl. No. 14/448,843, mailed on Mar. 29, 2016, 5 pages.

International Search Report and Written Opinion received for PCT Patent Application No. PCT/US2012/053221, mailed on Mar. 8, 2013, 15 pages.
Aklujkar et al., "The Genome Sequence of Geobacter Metallireducens: Features of Metabolism, Physiology and Regulation Common and Dissimilar to Geobacter sulfurreducens", BMC Microbiology, May 2009, 22 pages, vol. 9, No. 109, BioMed Central Ltd.
Aklujkar et al., "Geopilin [Geobacter bemidjiensis Bem]", Accession No. YP_002139394.1, 2010, 1 page.
Altschul et al., "Gapped BLAST and PSI-BLAST: A New Generation of Protein Database Search Programs", Nucleic Acids Research, Sep. 1997, pp. 3389-3402, vol. 25, No. 17, Oxford University Press.
Ausubel et al., "Current Protocols in Molecular Biology: Preparation and Analysis of DNA", John Wiley & Sons, Inc., © 2003, Chapter 2, Supplement 58, 2002,161 pages.
Ausubel et al., "Current Protocols in Molecular Biology: Informatics for Molecular Biologists", John Wiley & Sons, Inc., © 2003, Chapter 19, Supplement 70, 2002, 137 pages.
Ausubel et al., "Current Protocols in Molecular Biology", John Wiley & Sons, Inc., @ 2003. Section II (Supplement 41) and Section III (Supplement 44), 1998, 517 pages.
Balch et al., "Methanogens: Reevaluation of a Unique Biological Group", Microbiological Reviews, Jun. 1979, pp. 260-296, vol. 43, No. 2.
Bernard et al., "Tight Attachment of Chitin-Binding-Domain-Tagged Proteins to Surfaces Coated with Acetylated Chitosan", Analytical Biochemistry, 2004, pp. 278-283, vol. 327.
Bolivar et al., "Construction and Characterization of New Cloning Vehicles: II. A Multipurpose Cloning System", Gene, Nov. 1977, pp. 95-113, vol. 2, No. 2.
Chang et al., "Phenotypic Expression in *E. coli* of a DNA Sequence Coding for Mouse Dihydrofolate Reductase", Nature, Oct. 1978, pp. 617-624, vol. 275.
Chothia et al., "The Relation Between the Divergence of Sequence and Structure in Proteins", The EMBO Journal, Apr. 1986, pp. 823-826, vol. 5, No. 4.
Claverie et al., "Information Enhancement Methods for Large Scale Sequence Analysis", Computers Chem., Jun. 1993, pp. 191-201, vol. 17, No. 2.
Collinson et al., "Purification and Characterization of Thin, Aggregative Fimbriae from *Salmonella enteritidis*", Journal of Bacteriology, Aug. 1991, pp. 4773-4781, vol. 173, No. 15.
Cologgi et al., "Extraceullular Reduction of Uranium via Geobacter Conductive Pili as a Protective Cellular Mechanism", PNAS Early Edition, 2011, pp. 15248-15252, vol. 108, No. 37.
Copeland et al., "N-terminal Methylation [Geobacter metallireducens GS-15]", Accession No. YP_384358.1, 2005, 1 page.
Copeland et al., Pilin Domain-Contaning Protein [Pelobacter propionicus DSM 2379], Accession No. YP_901328.1, 2006, 1 page.
Coppi et al., "Development of a Genetic System for Geobacter sulfurreducens", Applied and Environmental Microbiology, Jul. 2001, pp. 3180-3187, vol. 67, No. 7.
Corpet, F. "Multiple Sequence Alignment with Hierarchical Clustering", Nucleic Acids Research, Nov. 1988, pp. 10881-10890, vol. 16, No. 22.
Cory et al., "Fluorescence Spectroscopy Reveals Ubiquitous Presence of Oxidized and Reduced Quinoes in Dissolved Organic Matter", Environmental Science and Technology, Nov. 2005, pp. 8142-8149, vol. 39, No. 21.
Cosert et al., "Electronic Characterization of Geobacter sulfurreducens Pilins in Self-Assembled Monolayers Unmasks Tunneling and Hopping Conduction Pathways", Phys. Chem. Chem. Phys., 2017, pp. 11163-11172, vol. 19.
Craig et al., "Type IV Pilus Structure by Cryo-Electron Microscopy and Crystallography: Implications for Pilus Assembly and Functions", Molecular Cell, Sep. 2006, pp. 651-662, vol. 23, No. 5.
De Boer et al., "The Tac Promoter: A Functional Hybrid Derived from the TRP and LAC Promoters", PNAS, Jan. 1983, pp. 21-25, vol. 80, No. 1.
Fasman, G. "Practical Handbook of Biochemistry and Molecular Biology" CRC Press, Inc., © 1989, 7 pages, table of contents.

(56) References Cited

OTHER PUBLICATIONS

Feliciano et al., "Molecular and Electronic Structure of the Peptide Subunit of Geobacter sulfurreducens Conductive Pili from First Principles", The Journal of Physical Chemistry A, Jul. 2012, pp. 8023-8030, vol. 116, No. 30.
Feliciano et al., "Structural and Functional Insights Into the Conductive Pili of Geobacter sulfurreducens Revealed in Molecular Dynamics Simulations", Phys. Chem. Chem. Phys., 2015, pp. 22217-22226, vol. 17.
Feng et al., "Progressive Sequence Alignment as a Prerequisite to Correct Phylogenetic Trees", Journal of Molecular Evolution, Aug. 1987, pp. 351-360, vol. 25, No. 4.
Ferrandon et al., "A Single Surface Tryptophan in the Chitin-Binding Domain from Bacillus circulans Chitinase A1 Plays a Pivotal Role in Binding Chitin and Can be Modified to Create an Elutable Affinity Tag", Biochimica et Biophysica Acta., Apr. 2003, pp. 31-40, vol. 1621.
Fong et al, "The Potential Role of Self-Cleaving Purification Tags in Commercial-Scale Processes", Trends in Biotechnology, 2010, pp. 272-279, vol. 28, No. 5.
Forero, A. "Properties and Applications of Self-Assembled Biomolecules in Nanostructured Biomimetic Interfaces", A Dissertation Submitted to Michigan State University, 2011, 54 pages, partial, appears to be cut off at p. 37.
Genbank Accession No. ZP_05310612.1, "Pilin Domain-containing Protein [*Geobacter* sp. M18]", Nov. 9, 2010, 1 page.
Goeddel et al., "Direct Expression in *Escherichia coli* of a DNA Sequence Coding for Human Growth Hormone", Nature, Oct. 1979, pp. 544-548, vol. 281.
Goeddel et al., "Synthesis of Human Fibroblast Interferon by *E. coli*", Nucleic Acids Research, Sep. 1980, pp. 4057-4074, vol. 8, No. 18.
Greenfield, N. "Using Circular Dichroism Spectra to Estimate Protein Secondary Structure", Nature Protocols, 2006, pp. 2876-2890, vol. 1, No. 6.
Guzman et al., "FtsL, an Essential Cytoplasmic Membrane Protein Involved in Cell Division in *Escherichia coli*", Journal of Bacteriology, Dec. 1992, pp. 7716-7728, vol. 174, No. 23.
Guzman et al., "Tight Regulation, Modulation, and High-Level Expression by Vectors Containing the Arabinose Pbad Promoter", Journal of Bacteriology, Jul. 1995, pp. 4121-4130, vol. 177, No. 14.
Haldimann et al., "Use of New Methods for Construction of Tightly Regulated Arabinose and Rhamnose Promoter Fusions in Studies of the *Escherichia coli* Phosphate Regulon", Journal of Bacteriology, Mar. 1998, pp. 1277-1286, vol. 180, No. 5.
Hay et al., "Protein Engineering of Cytochrome b562 for Quinone Binding and Light-Induced Electron Transfer", PNAS, Dec. 2004, pp. 17675-17680, vol. 101, No. 51.
Henikoff et al., "Amino Acid Substitution Matrices from Protein Blocks", PNAS, Nov. 1992, pp. 10915-10919, vol. 89. No. 22.
Higgins et al., "Clustal: A Package for Performing Multiple Sequence Alignment on a Microcomputer", Gene, Dec. 1988, pp. 237-244, vol. 73, No. 1.
Higgins et al., "Fast and Sensitive Multiple Sequence Alignments on a Microcomputer", Computer Applications in the Biosciences, Feb. 1989, pp. 151-153, vol. 5, No. 2.
Huang et al., "Parallelization of a Local Similarity Algorithm", Computer Applications in the Biosciences, Feb. 1992, pp. 155-165, vol. 8, No. 2.
Kyte et al., "A Simple Method for Displaying the Hydropathic Character of a Protein", Journal of Molecular Biology, May 1982, pp. 105-132, vol. 157, No. 1.
Leang et al., "Genome-wide Analysis of the RpoN Regulon in Geobacter sulfurreducens", BMC Genomics, Jul. 2009, pp. 1-19, vol. 10, No. 331.
Leang et al., "Alignment of the c-Type Cytochrome OmeS Along Pili of Geobacter sulfurreducens", Applied and Environmental Microbiology, Jun. 2010, vol. 76, No. 12, 19 pages.

Li et al., "Fed-Batch Fermentor Synthesis of 3-Dehydroshikimic Acid Using Recombinant *Escherichia coli*", Biotechnoloy and Bioengineering, Jul. 1999, pp. 61-73, vol. 64, No. 1.
Lovley et al., "Rapidly Growing Rumen Methanogenic Organism That Synthesizes Coenzyme M and Has a High Affinity for Formate", Applied and Environmental Microbiology, Jul. 1984, pp. 81-87, vol. 48, No. 1.
Lovley et al. "Novel Mode of Microbial Energy Metabolism: Organic Carbon Oxidation Coupled to Dissimilatory Reduction of Iron or Manganese", Applied and Environmental Microbiology, Jun. 1988, pp. 1472-1480, vol. 54, No. 6.
Lucas et al., "Pilin [*Geobacter* sp. M21]", Accession No. YP_003021449.1, 2009, 1 page.
Lucas et al., "Pilin Domain-Containing Protein [Geobacter lovleyi SZ]", Accession No. YP_001952332.1, 2008, 1 page.
Lutz et al., "Independent and Tight Regulation of Transcriptional Units in *Escherichia coli* via the LacR/O, the TetR/O and AraC/11-12 Regulatory Elements", Nucleic Acids Research, Mar. 1997, pp. 1203-1210, vol. 25, No. 6.
Malhotra, A. "Chapter 16: Tagging for Protein Expressions", Methods in Enzymology, © 2009, pp. 239-258, vol. 463.
Means et al., "Chemical Modification of Proteins", Holden-Day, Inc., San Francisco, © 1971, 7 pages, table of contents.
Meinkoth et al., "Hybridization of Nucleic Acids Immobilized on Solid Supports", Analytical Biochemistry, May 1984, pp. 267-284, vol. 138, No. 2.
Menzella et al., "Novel *Escherichia coli* Strain Allows Efficient Recombinant Protein Production Using Lactose as Inducer", Biotechnology and Bioengineering, Jun. 2003, pp. 809-817, vol. 82, No. 7.
Methe et al., "Genome of Geobacter sulfurreducens: Metal Reduction in Subsurface Environments", Science, Dec. 2003, pp. 1967-1969, vol. 302.
Methe et al., "Hypothetical Protein GSU1496 [Geobacter sulfurreducens PCA]", Accession No. NP_952547.1, 2003, 1 page.
Mihalyi, E., "Numerical Values of the Absorbances of the Aromatic Amino Acids in Acid, Neutral, and Alkaline Solutions", Journal of Chemical and Engineering Data, Apr. 1968, pp. 179-182, vol. 13, No. 2.
Mikayama et al., "Molecular Cloning and Functional Expression of a cDNA Encoding Glycosylation-Inhibiting Factor", PNAS, Nov. 1993, pp. 10056-10060, vol. 90. No. 21.
Nagarajan et al., "De Novo Assembly of the Complete Genome of an Enhanced Electricity-Producing Variant of Geobacter sulfurreducens Using Only Short Reads", PLoS ONE, Jun. 2010, vol. 5, No. 6, 9 pages.
Nagarajan et al., "Type IV Pilin PIIA [Geobacter sulfurreducens KN400]", Accession No. ADI84335.1, 2010, 1 page.
Needleman et al., "A General Method Applicable to the Search for Similarities in the Amino Acid Sequence of Two Proteins", Journal of Molecular Biology, Mar. 1970, pp. 443-453, vol. 48, No. 3.
Pearson et al., "Improved Tools for Biological Sequence Comparison", PNAS, Apr. 1988, pp. 2444-2448, vol. 85, No. 8.
Provencher et al., "Estimation of Globular Protein Secondary Structure from Circular Dichroism", Biochemistry, Jan. 1981, pp. 33-37, vol. 20, No. 1.
Reguera et al., "Extracellular Electron Transfer via Microbial Nanowires", Nature, Jun. 2005, pp. 1098-1101, vol. 435.
Reguera et al., "Possible Nonconductive Role of Geobacter sulfurreducens Pilus Nanowires in Biofilm Formation", Journal of Bacteriology, Mar. 2007, pp. 2125-2127, vol. 189, No. 5.
Reguera, G. "Harnessing the Power of Microbial Nanowires", Microbial Biotechnology, pp. 979-994, vol. 11, 2018.
Rudinger, J. "Characteristics of the Amino Acids as Components of a Peptide Hormone Sequence", National Institute for Medical Research, Jun. 1976, 9 pages.
Sambrook et al., "Molecular Cloning—A Laboratory Manual", 3rd Edition, Chapter 2, Cold Spring Harbor Laboratory Press, © 2001, 138 pages, chapter 2.
Siegele et al., "Gene Expression From Plasmids Containing the araBAD Promoter at Subsaturating Inducer Concentrations Represents Mixed Populations", PNAS, Jul. 1997, pp. 8168-8172, vol. 94, No. 15.

(56) References Cited

OTHER PUBLICATIONS

Smith et al., "Comparison of Biosequences", Advances in Applied Mathematics, 1981, pp. 482-489, vol. 2, No. 4.

Speers et al., "Genetic Identification of a PilT Motor in Geobacter sulfurreducens Reveals a Role for Pilus Retraction in Extracellular Electron Transfer", Frontiers in Microbiology, Oct. 2016, vol. 7, 17 pages.

Sreerama et al., "Estimation of Protein Secondary Structure from Circular Dichroism Spectra: Comparison of Contin, Selcon, and CDSSTR Methods with an Expanded Reference Set", Analytical Biochemistry, Dec. 2000, pp. 252-260, vol. 287, No. 2.

Steidl et al., "Mechanistic Stratification in Electroactive Biofilms of Geobacter sulfurreducens Mediated by Pilus Nanowires", Nature Communications, Aug. 2016, pp. 1-10, vol. 7.

Tijssen, P. "Overview of Principles of Hybridization and the Strategy of Nucleic Acid Probe Assays", Chapter 2, Laboratory Techniques in Biochemistry and Molecular Biology—Hybridization with Nucleic Acid Probes, Part 1, © 1993, 11 pages, table of contents.

Van Stokkum et al., "Estimation of Protein Secondary Structure and Error Analysis from Circular Dichroism Spectra", Analytical Biochemistry, Nov. 1990, pp. 110-118, vol. 191, No. 1.

Veazey et al., "Microbial Nanowire Electronic Structure Probed by Scanning Tunneling Microscopy", Biophysical Journal, 2010, vol. 98, No. 3, 1 page.

Veazey et al., "Electronic Properties of Conductive Pili of the Metal-Reducing Bacterium Geobacter sulfurreducens Probed by Scanning Tunneling Microscopy", Physical Review E, Dec. 2011, pp. 060901-1-060901-4, vol. 84.

Walker, J. "The Protein Protocols Handbook", Parts II and III, Second Edition, Humana Press Inc., © 2002, 400 pages.

Wallace et al., "Modern Techniques for Circular Dichroism and Synchrotron Radiation Circular Dichroism Spectroscopy", Advances in Biomedical Spectroscopy, IOS Press, © 2009, vol. 1, 245 pages.

Whitmore et al., "DICHROWEB, an Online Server for Protein Secondary Structure Analyses from Circular Dichroism Spectroscopic Data", Nucleic Acids Research, Jul. 2004, pp. W668-W673, vol. 32.

* cited by examiner

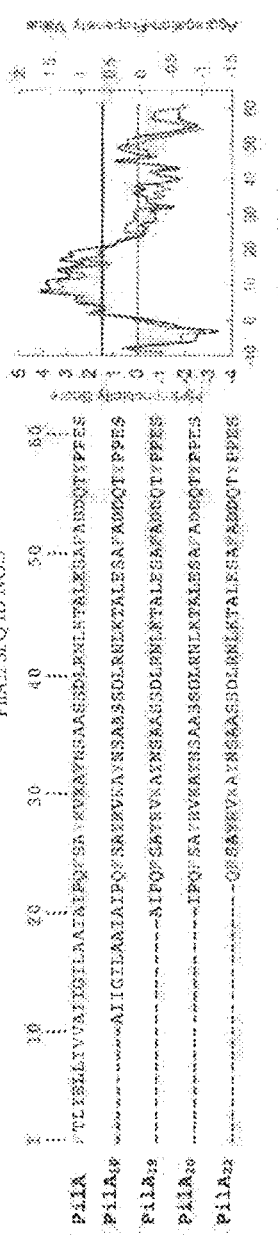
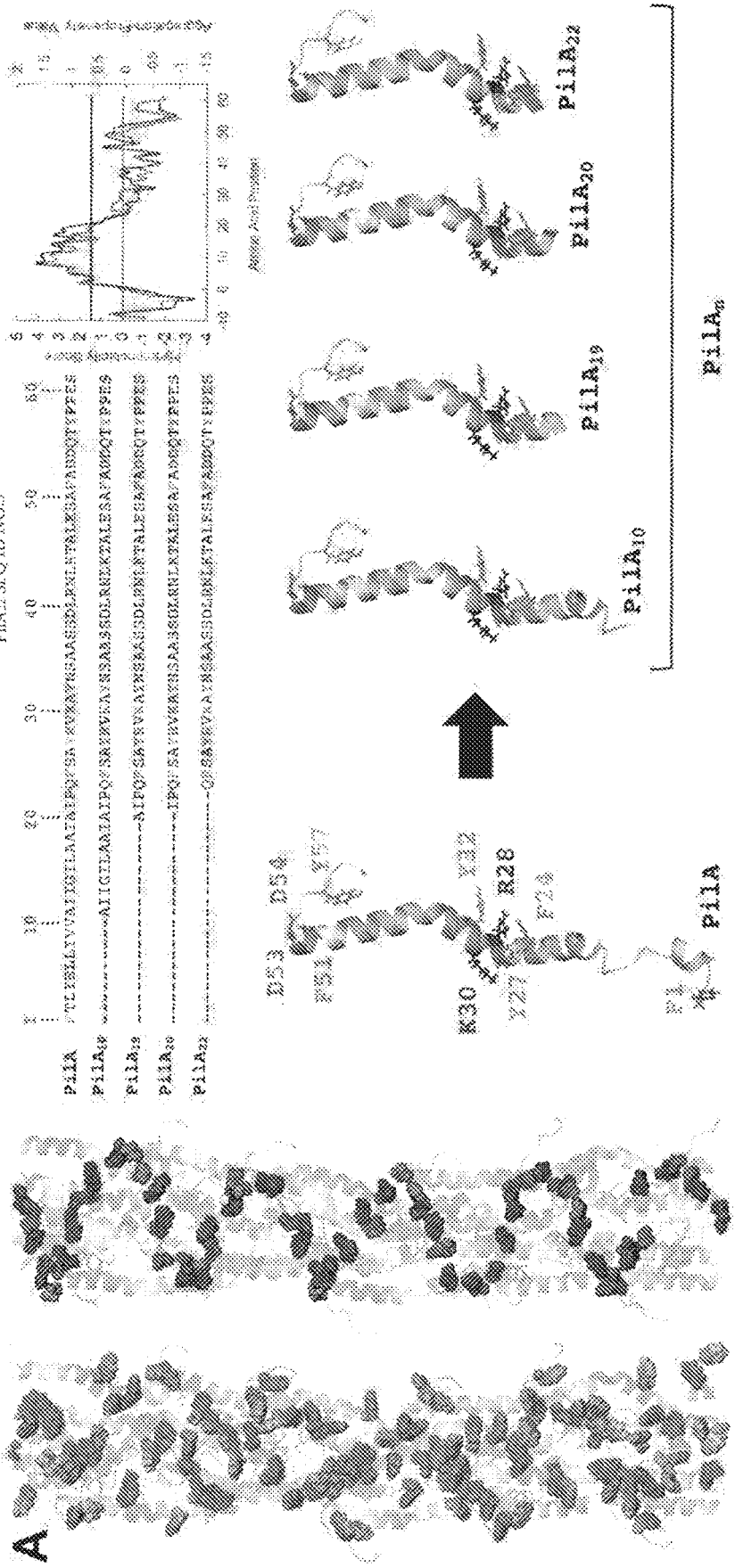
FIG. 1A
FIG. 1B
FIG. 1C
FIG. 1D

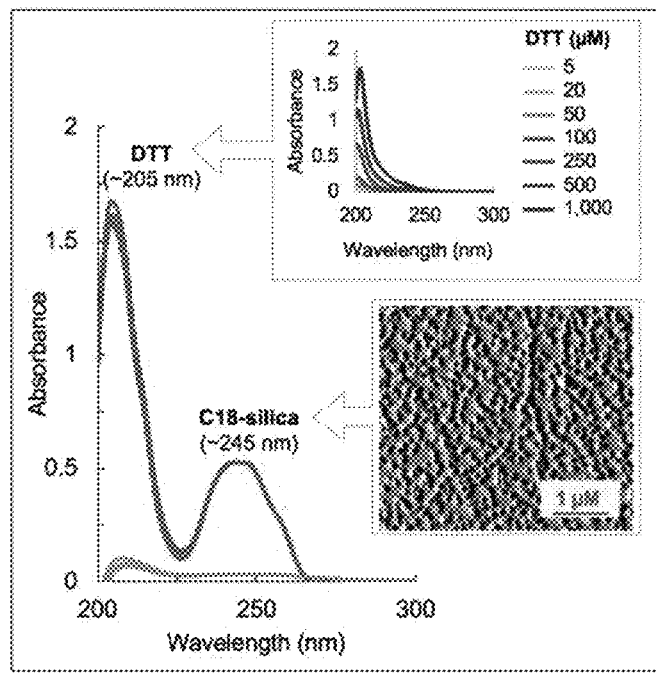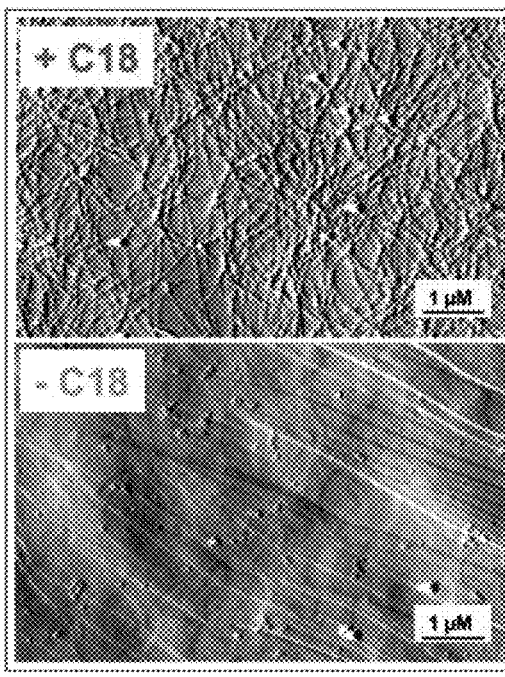
FIG. 6A
FIG. 6B
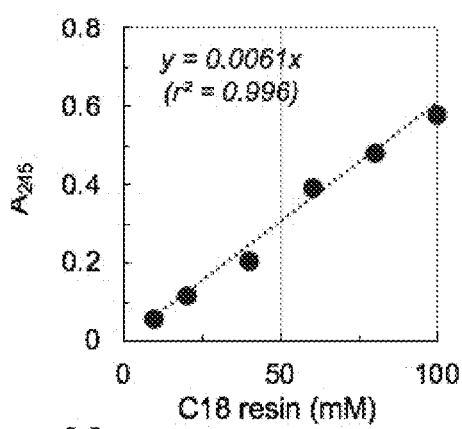
FIG. 6C
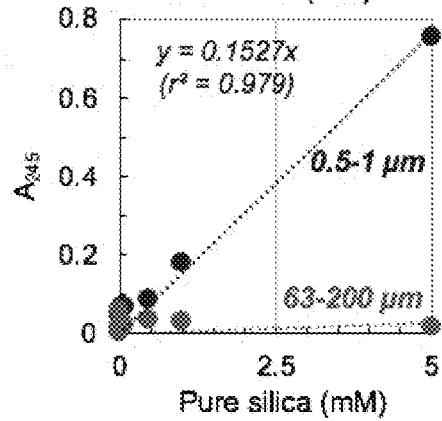
FIG. 6D

METHOD FOR PROTEIN NANOWIRE SYNTHESIS AND TUNABLE CONTROL OF NANOWIRE LENGTH

CROSS-REFERENCE TO RELATED APPLICATIONS

The present application is a divisional of U.S. patent application Ser. No. 16/995,163, filed on Aug. 17, 2020, which claims benefit under 35 U.S.C. 119(e) of U.S. Provisional Application Ser. No. 62/896,179, filed on Sep. 5, 2019.

INCORPORATION OF SEQUENCE LISTING

The sequence listing that is contained in the file named "Sequence_Listing_M2890092US2.xml" which is 18 kilobytes as measured in Microsoft Windows operating system and was created on Jan. 3, 2024, and is filed electronically herewith and incorporated by reference.

STATEMENT OF GOVERNMENT RIGHTS

This invention was made with government support under MCB1021948 and 1629439 awarded by the National Science Foundation, and under ES017052 awarded by the National Institutes of Health. The government has certain rights in the invention.

BACKGROUND

Semiconductor electronics have exhibited a sustained exponential decrease in size and cost with a similar increase in performance over the last thirty years. While such progress is expected to continue, the economics and/or physical barriers of continued use of silicon for increasingly small and more powerful devices will ultimately pose a challenge. Moreover, increases in pollution have been tied with increased energy consumption for at least the last several hundred years. Accelerated global warming and environmental degradation make the development of alternative energy sources an urgent priority. The world therefore needs new sources of energy and new materials for use in fuel cells and nanoelectronic devices.

SUMMARY

Microbes have the potential to address the problems of pollution, the need for clean affordable energy and the need for new nanoelectronic materials. The present description relates to synthesis of microbial nanowires that conduct electricity. Such nanowires are made from peptides inspired in microbial pilins such as modified PilA peptides, which are the structural subunit of microbial protein appendages known as pili. In one embodiment, the description herein relates to expression of modified PilA peptides in a recombinant system and to the formation of functional pilin nanowires using the modified PilA peptides. In some embodiments, the nucleic acids encoding the pilin peptides are recombinantly modified, expressed and isolated. The isolated PilA peptides can then be assembled to form conductive pilin nanowires. In one embodiment, the modified PilA peptides are synthesized PilA peptides. The ability for modified PilA peptides, such as truncated PilA peptides, to form functional nanowires can enable production of large quantities of conductive pilin nanowires.

In one aspect, the present description relates to methods for synthesizing protein nanowires from modified PilA peptides. The modified PilA peptides may be recombinant PilA peptides. The modified PilA peptides may be truncated PilA peptides. The truncated PilA peptides can include peptides comprising an amino acid sequence selected from SEQ ID NO:1-5. In some embodiments, the amino acid sequence of the disclosed modified PilA peptides may be genetically or chemically modified so the nanowires formed from the modified PilA peptide has electrical conductivity or other desirable activity. In other embodiments, the nanowires formed from the modified PilA peptides can have modified adhesive or coupling properties relative to naturally occurring nanowire polypeptides.

Another aspect of the invention is a pilus or pili that includes such a modified nanowire polypeptide. Further aspects of the invention use the disclosed pilin nanowires in devices and for soluble metal remediation.

In one embodiment, the present description includes a method of synthesizing protein nanowires. The method can include providing purified peptide building blocks. In one embodiment, the peptide building blocks may be isolated from a recombinant host. The method can include suspending the purified peptide building blocks in an assembly buffer. The method can include forming an assembly composition by adding a hydrophobe to the assembly buffer and peptide building blocks to trigger self-assembly of the peptide building blocks. The method can include increasing molecular crowding by evaporation of a volume of the assembly buffer in the assembly composition to facilitate hydrophobe guided assembly of conductive nanowires.

In one embodiment, the method can further comprise conducting one or more elongation cycles to promote fiber formation. In one embodiment, the elongation cycle can include providing additional peptide building blocks by refeeding the assembly composition. In one embodiment, the elongation cycle may include providing additional hydrophobe into the assembly composition. In one embodiment, the elongation cycle can also include mixing the assembly composition and evaporating the assembly buffer from the assembly composition.

In one embodiment, the method can comprise conducting about 4 cycles of elongation. In one embodiment, the hydrophobe is octadecane. In one embodiment the octadecane is provided in surface-constrained form.

In one embodiment, the hydrophobe is added to the assembly composition by loading the peptide building blocks into a column comprising particles and eluting the peptide building blocks into the assembly buffer, wherein the elution results in the co-elution of a portion of the particles of the column and the peptide building blocks into the assembly buffer and wherein the particles of the column are the hydrophobes in the assembly composition. In one embodiment, the hydrophobe is C18-silica particles.

In one embodiment, the peptide building blocks are recombinant modified PilA peptides. In one embodiment, the recombinant host is $E.\ coli$. In one embodiment, the peptide building blocks are truncated PilA peptides from $G.\ sulfurreducens$. In one embodiment, the peptide building blocks are $PilA_{19}$ peptides from $G.\ sulfurreducens$. In one embodiment, the peptide building blocks are truncated $PilA_n$ peptides, wherein the truncated $PilA_n$ peptides have the amino acid sequences selected from the group consisting of SEQ ID NO:2, SEQ ID NO:3, SEQ ID NO:4, and SEQ ID NO:5.

In one embodiment, the nanowires formed have a length from about 0.5 µm to about 10 µm. In some embodiments, the nanowires may have a length from about 2 μm to about 8 μm or from about 4 μm to about 7 μm, further including any range therebetween.

In one embodiment, the present description includes a composition comprising synthesized protein nanowires. The protein nanowires may be recombinant protein nanowires. In one embodiment, the nanowires can include peptide building blocks. The peptide building blocks may be derived from PilA peptide. The peptide building blocks may be modified PilA peptides. The peptide building blocks may be recombinant peptide building blocks. In one embodiment, the nanowires have a length of from about 1 μm to about 10 μm.

In one embodiment, the peptide building blocks are truncated PilA peptides. In one embodiment, the peptide building blocks are $PilA_{19}$ peptides. In one embodiment, the nanowires have a length from about 0.5 μm to about 10 μm or from about 5 μm to about 7 μm, further including any range therebetween.

In one embodiment, the nanowires have an average diameter of from about 1 nm to about 3 nm. In one embodiment, the nanowires have an average diameter of about 2 nm. In one embodiment, the nanowires have a Circular Dichroism (CD) profile with a 222 nm/208 nm intensity ratio of from about 0.7 to about 0.9. In one embodiment, the nanowires have a CD profile with a 222 nm/208 nm intensity ratio from about 0.9 to about 2. In one embodiment, the nanowires have a CD profile with a 222 nm/208 nm intensity ratio about 2 or higher.

BRIEF DESCRIPTION OF THE DRAWINGS

FIG. 1A is a model diagram of the molecular structure of a *Geobacter sulfurreducens* (Gsu) pilus fiber optimized via molecular dynamics (MD) showing aromatic residues (phenylalanines and tyrosines in the diagram on the left) and charged amino acids involved in salt bridges (acidic and basic in the diagram on the right).

FIG. 1B is a diagram of the alignment of the amino sequence of the PilA monomer and the N-terminus truncated $PilA_n$ derivatives.

FIG. 1C is a graph that shows Kyte-Doolittle and AGGR-ESCAN plots and analyses of the PilA pilin with signal peptide (prepilin) and cut-off values (horizontal lines) of hydrophobicity and aggregation potential scores.

FIG. 1D is a model via MD of the mature PilA pilin and $PilA_n$ derivatives highlighting aromatic and charge amino acids in FIG. 1A.

FIG. 6A is plot of the UV-Vis spectra showing the effect of C18-column wash on nucleator concentration. UV-vis spectra of eluants from triplicate C18-columns washed with 5 ml (dark color; optimal protocol for $PilA_{19}$ fiber formation) or 18 ml (light color; extended wash preventing $PilA_{19}$ fiber formation) of $ddH_2O$ prior to buffer exchange with assembly buffer. Reduced washes produce the spectral peaks for DTT (~205 nm) and silica (~245 nm). The silica peak is produced by C18-silica particles 25-50 nm in diameter (AFM image in inset).

FIG. 6B are images showing the effect of C18-silica hydrophobe on $PilA_{19}$ fiber formation. Tapping mode AFM showing optimal fiber formation in the presence (top) but not in the absence (bottom) of the C18-silica particles.

FIG. 6C is a plot of standard curves of absorbance at 245 nm of silica in solutions made with assembly buffer and the column's C18-silica resin.

FIG. 6D is a plot of standard curves of absorbance at 245 nm of silica in solutions made with assembly buffer and pure silica particles of sizes similar to those of the column's resin (63-200 μm) (FIG. 6C) and eluted particles (0.5-1 μm).

FIGS. 7A-7B are images of C18-columns washed with 5 ml (FIG. 7A), 15 ml (FIG. 7B) or 30 ml (FIG. 7C) of $ddH_2O$ on $PilA_{19}$ fiber formation to reduce the amount of loosely-bound C15-silica particles co-eluting with $PilA_{19}$ during the buffer column exchange step. FIGS. 7D-7F are images of $PilA_{19}$ fiber formation of a buffer-only control. The eluents were subjected to the evaporation induced assembly protocol and samples deposited on HOPG were imaged with an AFM operated in tapping mode.

FIGS. 10A and 10B are AFM amplitude images of recombinant (FIG. 10A) and native (FIG. 10B) pili on HOPG (scale bars, 200 nm) with FIG. 10C and FIG. 10D showing representative I-V curves of their CP-AFM transversal conductivity (average, in black). FIGS. 10E and 10F are room temperature STM topographic images of untreated (FIG. 10E) or chemically-fixed (FIG. 10F) recombinant pili (0.5 V, 350 picoampere (pA); scale bar, 100 nm). FIGS. 10G-10H are average I-V tunneling spectra of 2 sequential measurements for each of two pilus regions in untreated (black) and fixed (gray) samples (FIG. 10G). FIG. 10H shows differential conductance (dI/dV) curves of the untreated and chemically treated pili, calculated as the numerical derivative of the I-V curves shown in FIG. 10G.

DESCRIPTION OF THE EMBODIMENTS

Figure 2:
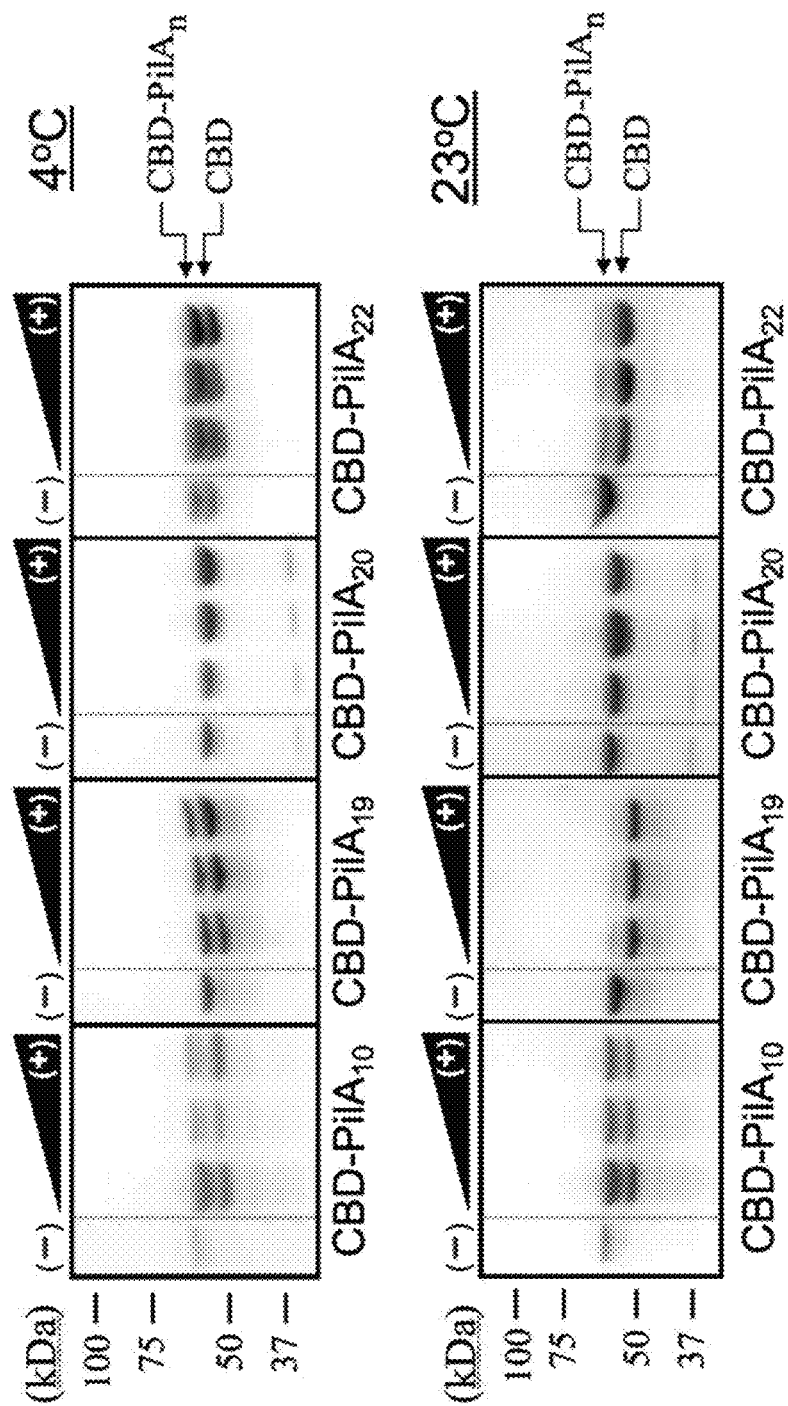
FIG. 2 is a photograph of the effect of temperature and incubation time with DTT inducer on cleavage of the $PilA_n$ peptides from the CBD module. The full fusion (CBD-$PilA_n$) and peptide-free CBD proteins bound to the chitin beads were solubilized by boiling with 1% SDS and separated in a 7.5% glycine SDS-PAGE. The approximate migration of the two bands is indicated in reference to molecular mass standards (numbers at left). Lanes: no DTT (−) or incubation with DTT (+) for 24, 48 or 72 h. The ratio of the lower band (CBD) over the slow migrating band (CBD-$PilA_n$) serves as a proxy of cleavage efficiency.

In the following detailed description, the embodiments are described in sufficient detail to enable those skilled in the art to practice them, and it is to be understood that other embodiments may be utilized and that chemical and procedural changes may be made without departing from the spirit and scope of the present subject matter. The following detailed description is, therefore, not to be taken in a limiting sense, and the scope of the embodiments is defined only by the appended claims.

The embodiments described herein can include a novel method for synthesizing protein nanowires. The protein nanowires may be synthesized using recombinant peptide building blocks. In one embodiment, the peptide building blocks can be derived from the conductive pilin peptide of the electrically active bacterium *Geobacter sulfurreducens*. The synthesis of nanowires can include nucleation and elongation steps for efficient peptide self-assembly and control of nanowire length. The method can include addition of a hydrophobe. The hydrophobe may be, for example, octadecane, provided in aqueous solution. The hydrophobe may also be materials such as functionalized silica beads. The hydrophobe can trigger the self-assembly of the peptides and fiber formation. The method may also include increasing molecular crowding via evaporation to facilitate hydrophobe-guided nucleation and assembly of the peptides into conductive protein fibers. Additional refeeding steps with mixing may be used to control the length of the nanowires and the yields of nanowires. The method can yield protein nanowires that retain the biochemical and electronic properties of the native protein nanowires (pili) produced by *Geobacter* cells even under chemical fixation, a critical consideration for integration in electronic devices.

Unlike the native protein nanowires, synthesized protein nanowires can be mass-produced in a scalable process. This process may use a recombinant host (e.g., *E. coli*) to produce the genetically engineered peptide building blocks and can rely on molecular crowding in the presence of a hydrophobe to induce peptide self-assembly into protein nanowires of defined length. This can result in design and mass production of generations of protein nanowires for custom applications. For example, if only currently available technologies were employed, the costs of building the necessary manufacturing facilities will become prohibitive due to the shrinking size of devices, heat dissipation problems due to closely packed structures, non-uniformity in dopant and conductive materials, and high electric fields that may lead to a cascade of breakdown events within closely packed components.

Various terms are defined herein. See also definitions in U.S. Pat. Nos. 9,716,287 and 10,074,867, both of which are incorporated herein by reference. In case of a conflict in the meaning of various terms, the definitions provided herein prevail.

The terms "preferred" and "preferably", "example" and "exemplary" refer to embodiments that may afford certain benefits, under certain circumstances. However, other embodiments may also be preferred or exemplary, under the same or other circumstances. Furthermore, the recitation of one or more preferred or exemplary embodiments does not imply that other embodiments are not useful and is not intended to exclude other embodiments from the inventive scope of the present disclosure.

The singular forms of the terms "a", "an", and "the" as used herein include plural references unless the context clearly dictates otherwise. For example, the term "a tip" includes a plurality of tips.

Reference to "a" chemical compound refers one or more molecules of the chemical compound, rather than being limited to a single molecule of the chemical compound. Furthermore, the one or more molecules may or may not be identical, so long as they fall under the category of the chemical compound.

The terms "at least one" and "one or more of" an element are used interchangeably and have the same meaning that includes a single element and a plurality of the elements, and may also be represented by the suffix "(s)" at the end of the element.

The terms "about" and "substantially" are used herein with respect to measurable values and ranges due to expected variations known to those skilled in the art (e.g., limitations and variability in measurements).

The terms "and/or" means one or all of the listed elements or a combination of any two or more of the listed elements.

The terms "comprises," "comprising," and variations thereof are to be construed as open ended—i.e., additional elements or steps are optional and may or may not be present.

The term "polypeptide" as used herein refers to at least two amino acid residues connected as a chain via covalent bonds such as peptide bonds, and can be recombinant polypeptides, natural polypeptides or synthetic polypeptides. The terms "polypeptide," "peptide" and "protein" are used interchangeably herein The terms "recombinant polypeptide" and "recombinant peptide" as used herein refers to a manipulated form of a polypeptides encoded by recombinant DNA which has been cloned in a foreign expression system to support the expression of the exogenous gene.

The term "peptide building blocks" as used herein refers to peptides that serve as the units for assembly into larger protein complexes such as fibers and/or nano wires. The peptide building blocks can be recombinant peptides and/or synthesized peptides. In one exemplary embodiment, the peptide building blocks are modified PilA peptides.

The term "fibers" as used herein refers to complexes of peptide building blocks that associate to form filamentous supramolecular protein structures. Fibers may or may not transport charges.

The term "nanowires" as used herein refers to complexes of pilin peptides that form conductive fiber assemblies. Nanowires have fiber-like geometry and transport charges.

The term "synthesized nanowire" as used herein refers to nanowires formed by purified pilin peptide(s). The pilin peptides may be synthesized such as by chemical methods. The pilin peptides may be synthesized by recombinant methods. The pilin peptides may be encoded by recombinant DNA which has been cloned in a foreign expression system to support the expression of the exogenous gene and form recombinant peptides. Synthesized nanowires in the present description may have modified pilin peptides relative to naturally occurring nanowires.

The term "recombinant nanowire" as used herein refers to nanowires formed by pilin peptide(s) encoded by recombinant DNA which has been cloned in a foreign expression system to support the expression of the exogenous gene. Recombinant nanowires in the present description may have modified pilin peptides relative to naturally occurring nanowires.

The term "genetically engineered" as used herein refers to a manipulated form of a polypeptide or a peptide encoded by recombinant DNA which has been cloned in a foreign expression system to support the expression of the exogenous gene.

The term "pilin peptides" or "PilA peptides" as used herein refers to PilA peptides. The term "pilin peptides" as used herein includes modified PilA peptides derived from the naturally occurring PilA peptides.

The term "derived" as used herein refers to modified peptides or genes relative to the naturally occurring peptide or gene. A modified or genetically engineered PilA peptide derived from naturally occurring PilA peptide has from about 10% identity to about 99% identity to the naturally occurring PilA peptide, or at least from about 10% identity to about 99% identity to the naturally occurring identity. The modified PilA peptide can keep the helical structure and assembly. The conductivity of the modified PilA peptide can depend on the presence of the aromatic and charged residues and formation of salt bridges between neighboring peptides.

The term "modified PilA peptides" as used herein refers to pilin peptides that have one or more amino acids that are different compared to the naturally occurring PilA polypeptide. Modified PilA peptides may have one more amino acids that are substituted and/or deleted or truncated compared to the naturally occurring PilA polypeptide.

The term "truncated PilA peptides" or "PilA$_n$" as used herein refers to pilin peptides that have one or more amino acids deleted compared to the naturally occurring PilA polypeptide. Examples of truncated PilA peptides can include PilA$_{10}$, PilA$_{19}$, PilA$_{20}$, PilA$_{22}$ and the like.

The term "PilA$_{19}$" as used herein refers to a PilA peptide that has the first 19 amino acids from the N-terminus of the PilA polypeptide deleted.

The term "pilus" (singular) or "pili" (plural) as used herein refers to complexes formed by pilin peptides and are electrically conductive.

The term "protein nanowires" as used herein refers to the complex of polypeptides formed into filaments that are electrically conductive.

The term "pilus nanowires" as used herein refers to filaments that are electrically conductive and formed from PilA peptides, modified PilA peptides and/or truncated PilA peptides.

The term "assembly buffer" as used herein refers to a buffer that maintains peptide building blocks such as pilin peptides and modified pilin peptides in solution.

The term "assembly composition" as used herein refers to a composition that includes assembly buffer, peptide building blocks and a hydrophobe and can initiate self-assembly of the peptide building blocks into fibers.

The term "hydrophobe" as used herein refers to a molecule and/or material that is hydrophobic in nature and can serve as the nucleation site for the self-assembly of the peptide building blocks. Hydrophobes can be materials that can be coated with hydrophobic molecules to generate materials with hydrophobic characteristics.

The term "bottom-up fabrication" as used herein refers to synthesized protein nanowires.

The term "tunable control" as used herein refers to the ability to adjust experimental parameters to modify the characteristics of the material.

The term "substantial identity" as used herein refers to a peptide, protein or nucleic acid comprises a sequence with from about 10 to about 100% sequence identity to a reference sequence.

The term "biofilm" as used herein refers to a community of microbes particularly bacteria attached to a surface with the community members being contained or protected by a self-generated extracellular polymeric matrix or EPS.

The term "substrate" as used herein refers to a substance to which another substance binds or connects.

The term "conductance" refers to a material property whereby electrons migrate through the material in response to an applied voltage (difference in electrical potential) across the material. The rate of electron migration (charge/time) is the electrical current passing through the material. Materials that exhibit conductance are referred to as conductors.

In general, amino acids can be placed into three main classes: hydrophilic amino acids, hydrophobic amino acids and cysteine-like amino acids, depending primarily on the characteristics of the amino acid side chain. These main classes may be further divided into subclasses. For example, some types of hydrophobic amino acids have aromatic side chains while other types of hydrophobic amino acids do not have aromatic side chains. Moreover, aromatic amino acids can have functional groups that provide a more hydrophilic character and that permit acceptance and transport of electrons (e.g., tyrosine). In general, the hydrophilic and/or aromatic amino acids have a more direct role in the electrical conductivity functions of the pilus nanowires.

Hydrophilic amino acids include amino acids having acidic, basic or uncharged polar side chains and hydrophobic amino acids include amino acids having apolar side chains. Apolar amino acids may be further subdivided to include, among others, aliphatic amino acids. The definitions of the classes of amino acids as used herein are as follows:

The term "hydrophobic amino acid" as used herein refers to an amino acid having a side chain that is uncharged at physiological pH and that is repelled by aqueous solution. Examples of genetically encoded hydrophobic amino acids include Ala, Ile, Leu and Val.

The term "aromatic amino acid" as used herein refers to a hydrophobic or hydrophilic amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4 tetrahydroisoquinoline-3-carboxylic acid, 4-chlorophenylalanine, 2-fluorophenylalanine, 3-fluorophenylalanine and 4-fluorophenylalanine.

The term "apolar amino acid" as used herein refers to a hydrophobic amino acid having a side chain that is generally uncharged at physiological pH and that is not polar. Examples of genetically encoded apolar amino acids include proline and methionine. Examples of non-encoded apolar amino acids include Cha.

The term "aliphatic amino acid" as used herein refers to an apolar amino acid having a saturated or unsaturated straight chain, branched or cyclic hydrocarbon side chain. Examples of genetically encoded aliphatic amino acids include Ala, Leu, Val and Ile.

The term "hydrophilic amino acid" as used herein refers to an amino acid having a side chain that is attracted by aqueous solution. Examples of genetically encoded hydrophilic amino acids include Ser and Lys.

The term "acidic amino acid" or "negatively charged amino acid" as used herein refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

The term "basic amino acid" as used herein refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

The term "polar amino acid" as used herein refers to a hydrophilic amino acid having a side chain that is uncharged at physiological pH, but where a bond in the side chain has a pair of electrons that are held more closely by one of the atoms involved in the bond. Examples of genetically encoded polar amino acids include asparagine and glutamine. Examples of non-genetically encoded polar amino acids include citrulline, N-acetyl lysine and methionine sulfoxide.

The term "cysteine-like amino acid" as used herein refers to an amino acid having a side chain capable of forming a covalent linkage with a side chain of another amino acid residue, such as a disulfide linkage. Typically, cysteine-like amino acids generally have a side chain containing at least one thiol (SH) group. An example of a genetically encoded cysteine-like amino acid is cysteine. Examples of non-genetically encoded cysteine-like amino acids include homocysteine and penicillamine.

As will be appreciated by those having skill in the art, the above classifications are not absolute. Several amino acids exhibit more than one characteristic property and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has an apolar character. Thus, while not strictly classified as a hydrophobic or an apolar amino acid, in many instances, cysteine can be used to confer hydrophobicity to a peptide.

Geobacteraceae bacteria and relatives in the order Desulfurococcales naturally produce protein filaments known as pili that are electrically conductive. For this reason, they are generally referred to as microbial or pilus nanowires. The pilus nanowires are protein filaments assembled on the cell envelope through the polymerization via hydrophobic interactions of a single peptide subunit, the pilin or PilA. The purified pili are electrically conductive. As the pili protrude outside the cell, other proteins, such as metalloproteins known as c-cytochromes, can bind the pili and may contribute to their conductivity and adhesive properties. However, biochemical analyses of the purified pili have demonstrated that they were conductive without being directly associated with metals or metalloenzymes. Furthermore, they lack any biological redox cofactors such as flavins and quinones. Thus, the conductivity of the nanowire protein filament is intrinsic to the pilin subunits in the assembly and is not due to any redox-active component that may associate with the nanowire polypeptide, such as metals, ions, contaminants, metalloenzymes, flavins or quinones.

The peptide subunit (or pilin) in the electrically conductive pili is encoded by the pilA gene of Geobacteraceae bacteria. The product of the pilA gene can generate a peptide or PilA or pilin that can polymerize via hydrophobic interactions to form the pilus. The Geobacteraceae pilus nanowire can electrically connect the cell with electron acceptors in its environment. This electronic connection can enable the cell to gain energy through the transfer of metabolically-generated electrons across electron transport proteins, such as c-cytochromes and other metalloproteins of the cell envelope, and through the pilus. The pilus can serve as the main electrical connection between the cell and extracellular acceptors such as Fe(III) oxides. *Geobacter sulfurreducens* can be naturally found in underground sediment where anaerobic conditions may require that an electron acceptor other than oxygen be employed and where minerals or other electron acceptors are commonly available. Thus, although *Geobacter sulfurreducens* can utilize oxygen as an electron acceptor, these bacteria can also transfer electrons from their pili to extracellular electron acceptors such as Fe(III) oxides, resulting in insoluble Fe(III) in the environment to be reduced to soluble Fe(II) and magnetic minerals of mixed Fe(III)-Fe(II) valence such as magnetite.

The pilus nanowires are dynamic filaments that can protrude and retract by polymerizing and depolymerizing the pilin subunits at the cell envelope. Thus, several pilin peptides can be assembled to make a pilus that can function as a nanowire. Extension and retraction events are powered, respectively, by the PilB (pilin polymerase) and PilT (pilin depolymerase) proteins, which belong to the secretion NTPase superfamily. The pilus nanowires can be predominantly helical in structure. In particular, they can be composed of an α-helical core spanning the hydrophobic N-terminus region that can promote pilin polymerization, and a short αβ-loop in the C-terminal region. Thus, the pilus nanowires from Geobacteraceae bacteria lack the long αβ-loop and extensive C-terminal globular head that other bacterial pili possess.

Pilin assembly can occur via hydrophobic interactions proceeding in a helical fashion that may help position electroactive amino acids by merging or bonding their atomic orbitals optimally so as to favor charge transport along and across the nanowire.

Bacteria in the genus *Geobacter* can produce conductive protein appendages of the Type IVa pilus class to discharge respiratory electrons onto extracellular electron acceptors such as ferric iron (Fe[III]) minerals and the uranyl cation as described in Reguera, G. et al. "Extracellular electron transfer via microbial nanowires". *Nature* 435, 1098-1101, (2005) and Cologgi, D. et al. "Extracellular reduction of uranium via *Geobacter* conductive pili as a protective cellular mechanism" *Proc Natl Acad Sci USA*, 108, 15248-15252 (2011), incorporated herein by reference in their entirety.

In Type IVa pili, *Geobacter* pili are also assemblies of primarily one peptide subunit (the pilin or PilA), though the structural pilins that make the conductive pili are shorter than canonical pilins and form an independent line of descent with pilins from other members the order Desulfurococcales. Assembly is however predicted to follow the conserved steps of other bacterial Type IV pili. In one embodiment, the bacteria *Geobacter sulfurreducens* synthesizes two pilin precursors (prepilins) with a long or a short signal peptide that interact for optimal pilin export to the membrane and coregulation of cytochrome export. The two prepilin isoforms carry the conserved recognition sequences needed for removal of the leader peptide and N-methylation of the mature peptide by a conserved PilD prepilin peptidase. A canonical Type IV pilus apparatus spanning the multilayered cell envelope assembles the pilins vertically on the inner membrane, exposing the base of the pilus fiber to the abundant periplasmic cytochromes to facilitate the discharge of respiratory electrons as described in Reguera, G. "Harnessing the power of microbial nanowires". *Microb Biotechnol* 11, 979-994, (2018), incorporated herein by reference in its entirety. Conductive pili isolated from *G. sulfurreducens* transport charges at rates (~1 billion electrons per second at biologically relevant voltages of 100 mV) two orders of magnitude greater than the cellular rates of respiration measured in iron oxide cultures.

Furthermore, each cell assembles numerous pili on one side of the cell, providing many conduits for the discharge of respiratory electrons. This biological strategy has been proposed to maximize access to the most bioavailable forms of iron oxides, which are dispersed in soils and sediments and rapidly transition into more crystalline and less bioavailable mineral forms abiotically. The reduction of iron oxides solubilizes part of the Fe(III) but also generates magnetite, a magnetic mineral of mixed Fe(III)/Fe(II) that remains bound to the pilus fibers.

Similarly, the pili retain the mononuclear uranium mineral phase formed during the reduction of the soluble uranyl cation as described in Cologgi, D. L. et al., "Extracellular reduction of uranium via *Geobacter* conductive pili as a protective cellular mechanism" *Proc Natl Acad Sci USA* 108, 15248-15252, (2011), incorporated herein by reference in its entirety. To enable new rounds of respiration, cells detach the reduced minerals by depolymerizing the pilins in a reaction energized by a conserved PilT ATPase (PilT4). The retraction of the pili stores the pilin peptides in the inner membrane, making them readily available for a new round of polymerization energized by a conserved PilB ATPase as described in Speers, A. M., et al. Genetic identification of a PilT motor in *Geobacter sulfurreducens* reveals a role for pilus retraction in extracellular electron transfer. *Frontiers in Microbiology* 7, 1578, (2016) and Steidl, R. et al. "Mechanistic stratification in electroactive biofilms of *Geobacter sulfurreducens* mediated by pilus nanowires". *Nat. Commun.* 7, 12217, (2016).

Antagonistic cycles of pilus protrusion and retraction by *Geobacter* cells can sustain respiration of extracellular electron acceptors. This is of special significance during the reduction of the uranyl cation, which is reductively precipitated by the pili outside the cell and prevented from traversing the outer membrane.

Studies in *G. sulfurreducens* have also helped define structural features of the *Geobacter* pilins that are critical for fiber formation and conductivity. The reduced size of *Geobacter* pilins (61 amino acids in *G. sulfurreducens* compared to 142-175 in other bacterial pilins) is the result of a carboxy-terminal (C-t) truncation in the conserved modular architecture of other Type IVa pilins. The globular head of Type IVa pilins, with its distinctive αβ-loop, anti-parallel β-sheet domain and D-region flanked by two conserved cysteines, is replaced in *Geobacter* pilins by a short, flexible random-coiled segment. This changes the chemistry of the pilus surface and exposes on the surface of the conductive pili amino acid ligands for metal binding and reduction Feliciano, G. T. et al. "Structural and functional insights into the conductive pili of *Geobacter sulfurreducens* revealed in molecular dynamics simulations" *Phys Chem Phys* 17, 22217-22226, (2015), incorporated herein by reference in its entirety. *Geobacter* pilins only retain the amino-terminal (N-t) α-helix (α1 domain), a conformation that promotes electronic coupling and charge transport.

The predominantly α-helical conformation of *Geobacter* pilins can increase the hydrophobicity and flexibility of the peptides compared to other pilins, allowing for tight pilin-pilin hydrophobic interactions during assembly and the formation of a strong yet flexible pilus fiber core. Proper alignment of pilins in the fiber core can be maintained by salt bridges between positively and negatively charged amino acids from neighboring α1-domains. Each pilin participates in the formation of two salt bridges (D53-K30 and D54-R28) that bend the peptide's mid-region and align the side chains of neighboring aromatic residues (phenylalanines and tyrosines) at distances optimal for charge transport.

FIG. 1A shows structural models of a pilus fiber and pilin peptide optimized in Molecular Dynamics (MD) simulations showing the aromatic residues and salt bridges that are critical for structural integrity and conductivity. MD simulations identify motions that bring some of the aromatic side chains of the pilins in the assembly within 3-5 Å distances, although these aromatic "contacts" never form at the same time, as in a metallic wire. The geometry of the aromatic contacts is also displaced, preventing π-π stacking and metallic-like conductivity. Yet the inter-aromatic distances and geometries of the aromatic side chains support a coherent mechanism of conductivity. Experimental validation of this prediction is available from the thermal activation of pilus conductivity demonstrated by scanning tunneling microscopy and the low charge mobility calculated for pilus fibers purified free of metal and organic contaminants, which cannot support a band conduction mechanism.

In one embodiment, the present description can include a method for synthesizing protein nanowires. The protein nanowires may be synthesized using peptide building blocks such as recombinant peptide building blocks. The recombinant peptide building blocks may be derived from the conductive pilin peptide of the electrically active bacterium *Geobacter sulfurreducens*. The method can include nucleation and elongation steps for efficient peptide self-assembly and control of nanowire length. The method can include addition of a hydrophobe such as octadecane, provided in aqueous solution or as functionalized silica particles. The method can include triggering the self-assembly of the peptides and fiber formation.

The method can include increasing molecular crowding via evaporation that can facilitate hydrophobe-guided nucleation and assembly of the pilin peptides into conductive protein fibers. The method can include additional refeeding steps with mixing that can be used to control the length of the nanowires and the yields of nanowires. In one embodiment, the method can yield protein nanowires that are conductive assemblies. In one embodiment, the method can yield protein nanowires that can retain at least some or all of the biochemical and electronic properties of the native protein nanowires (pili) produced by *Geobacter* cells. In one embodiment, the biochemical and electronic properties of the protein nanowires are maintained under chemical fixation. This can be an advantageous consideration for integration in electronic devices.

Microbial nanowires are described, for example, in U.S. Pat. No. 8,729,233 to Reguera et al., U.S. Pat. No. 8,846,890 to Reguera et al., and U.S. Pat. No. 9,409,955 to Reguera et al., which patents are incorporated herein by reference. Harnessing the unique properties of *Geobacter* pili will ultimately require protocols for their production and functionalization at high yields and costs at that are needed to satisfy market demands. Direct purification of conductive pili from native cells is achievable yet requires many purification steps to separate the pili from other cellular components. Moreover, cultivation of piliated cells under anaerobic conditions may not be easily scalable and yields of pure pili are low (in the mg range). Chemical synthesis of the naturally occurring peptides is possible, but random aggregation of the highly hydrophobic peptides reduces production yields and sample quality. Addition of solubility tags for recombinant expression of the naturally occurring pilin peptides also faces challenges because the high hydrophobicity of the peptide causes aggregation and toxic effects in heterologous hosts such as *Escherichia coli*.

In one embodiment, modified PilA peptides such as truncated versions of the PilA peptides at the N-terminus can overcome these challenges and enable their recombinant production when fused to suitable solubility modules. In one embodiment, thiolated versions of pilins engineered with a 19-amino acid N-t truncation can be successfully synthesized via recombinant techniques and can attach to and spontaneously assembly as a monolayer onto gold electrodes. The planar assembly of the thiolated pilins can be conductive via pilus-like mechanisms that alternate charge hopping through aromatic contacts and interchain tunneling across aromatic-free regions. The assembly can also expose the metal-binding ligands to the solvent and allows the monolayers to bind and reduce cationic metals, like the pilus fiber. In one embodiment, the thiolated pilins can retain the structural features and critical amino acids needed for self-assembly, conductivity and metal binding and reduction, making them attractive building blocks for the manufacturing of novel conductive biomaterials.

In one embodiment, a method of synthesizing protein nanowires is provided. The protein nanowires can be conductive nanowires. In one embodiment, the protein nanowires can be synthesized from peptide building blocks. In one embodiment, the peptide building blocks can include pilin peptides. The pilin peptides can be assembled to form pilus or pili nanowires that can be conductive. The nanowires formed from the peptide building blocks can be assembled to be conductive by transfer of electrons to a substrate such as iron cation, uranyl cation and the like.

In one embodiment, the method can include providing purified peptide building blocks. In one embodiment, the peptide building blocks can be recombinant peptides that have been expressed in a recombinant host system. The recombinant host system can be, for example, an *E. coli*-based host system. Other host systems may also be used and are within the scope of this description. In some embodiments, the recombinant peptide building blocks are overexpressed and can result in high amounts of peptide building blocks that can be isolated and/or purified. In one embodiment, the peptide building blocks can be synthesized, modified PilA peptides.

Bottom up fabrication of protein nanowires using recombinant pilin peptides using evaporation of a peptide containing solution was described in U.S. Pat. No. 9,601,227 to Reguera, G., et al. and incorporated herein by reference in its entirety.

The methods described herein include a hydrophobe, refeeding steps and/or reaction mixing to control the yields and length of the nanowire product. The methods described herein have been optimized to control the critical assembly, increase production yields of nanowires with custom lengths, and reduce sample-sample variability.

In one embodiment, the present description can include a method for scalable production and purification of recombinant pilins whose short N-t truncations can reduce their hydrophobicity without perturbing the structural and biochemical motifs critical for self-assembly and conductivity. The methods described herein also can include protocols for the bottom-up self-assembly of pilins into protein nanowires having structural and electronic characteristics similar to those of naturally occurring pili purified from *G. sulfurreducens*.

Methods for synthesis of nanowires will be described with reference to recombinant PilA peptides but it will be understood that synthesized PilA peptides may also be used in the methods for the nanowire synthesis and are within the scope of this description.

Unlike the synthesis of inorganic semiconductors, the bottom-up fabrication of pilin-based nanowires does not require complex crystal growth or the use of toxic metals. The methods described herein rely instead on a hydrophobe-triggered nucleation step and an elongation step that controls the length of the nanowire product. This self-assembly protocol, and the genetic amenability of the recombinant production system, offer opportunities to tune the properties of the peptide, and consequently, the functional characteristics of the resulting nanowire to design novel protein-based conductive nanomaterials for bioelectronics and other applications.

As shown in FIG. 1B, pilins can be designed with short truncations at the N-terminus of PilA pilin peptide to reduce the hydrophobicity of the peptides while preserving structural features and amino acids critical for self-assembly into conductive protein fibers. Computational analyses of the amino acid sequence of the native PilA pilin peptide (SEQ ID NO:1) of *G. sulfurreducens* via AGGRESCAN identified two regions in the peptide (residues 1-22 and 25-31) as having highest propensity to aggregate, with the first 10 amino acids contributing the most (FIG. 1B). In one embodiment, a truncation of about 11 amino acids can be necessary to reverse the sign of the GRAVY score of the PilA from positive to negative, a proxy for solubility. In one embodiment, the Kyte Doolittle plot can localize the highest hydrophobicity within the first 21 amino acids of PilA.

In some embodiments, truncations can be from about 10 amino acids to about 21 amino acids of native PilA peptide may lead to solubilization of the truncated PilA peptides and can facilitate the recombinant production of the synthesized nanowires. In some embodiments, these truncations can also be within the ranges that can preserve the aromatic and charged residues of the pilin required for fiber formation and conductivity (FIG. 1B). In one embodiment, the N-terminus region can be targeted to engineer pilin derivatives that can be suitable for recombinant expression using a previously described *E. coli* recombinant pilin production system Cosert, K. M., et al. "Electronic characterization of *Geobacter sulfurreducens* pilins in self-assembled monolayers unmasks tunneling and hopping conduction pathways". *Phys Chem Chem Phys* 19, 11163-11172, (2017), incorporated herein by reference in its entirety.

In one embodiment, the recombinant peptides or peptide building blocks can be expressed as a fusion polypeptide.

Nucleic acids encoding peptide building blocks such as truncated $PilA_n$ peptides, can be used for recombinant expression of the nanowire peptides, for example, by operably-linking the peptide building block nucleic acid to an expression control sequence within an expression vector, which can be introduced into a host cell for expression of the encoded peptide building blocks. The nucleic acids that encode peptide building blocks can also encode a fusion partner fused in-frame with the peptide building blocks, for example, to facilitate expression or purification of the peptide building blocks.

A nucleic acid molecule encoding a peptide building blocks can optionally be optimized for expression in a particular host cell and then operably linked to one or more transcription regulatory sequences, e.g., a promoter, one or more enhancers, a transcription termination sequence or a combination thereof, to form an expression cassette.

The peptide building blocks can also be expressed as fusion proteins. To express the peptide building blocks as a fusion protein, the nucleic acids that encode the peptide building blocks can also encode a fusion partner fused in-frame with the peptide building blocks. The fusion partner can serve as solubility and affinity tag to the peptide to facilitate its expression and purification. For example, fusion expression systems may add to the peptides a His tag (allowing purification on a Nickel column; Clontech Laboratories, Inc., Qiagen, Life Technologies Corp.); a MalE maltose binding protein, (New England Biolabs, allowing purification on an amylose column); a thioredoxin (allowing purification with a phenyl arsine oxide resin); a glutathione-S-transferase (GST, allowing purification with glutathione) and a chitin binding domain (allowing purification with chitin columns, New England Biolabs). By also encoding a signal peptide in-frame with the fusion protein some of these systems (e.g., MalE, His Tag™ (Roche)) can be adapted for periplasmic expression. Cytoplasmic expression can be achieved with these systems when no signal peptide is incorporated. The expressed fusion protein can contain a specific protease cleavage site for cleavage and removal of the fusion partner peptide. It may also include a self-splicing element such as an intein linker, which releases the peptide in the presence of a reducing agent such as DTT.

The type of fusion partner peptide can influence the ease or extent of expression and purification. For example, some types of fusion partner peptides may interfere with, or promote folding, aggregation, degradation, or solubility of the fusion protein. In general, a fusion partner peptide is selected that facilitates fusion protein expression, folding, solubility, purification or any combination thereof. In some embodiments, the fusion partner peptide can protect the fusion protein from proteolytic digestion or inhibit proteolytic degradation.

One example of a fusion partner peptide that is useful for expression and production of peptide building blocks is the chitin binding domain (CBD). The small size (about 5-7 kDa), substrate binding specificity and high avidity of CBDs for chitin has led to their utilization as affinity tags for immobilization of proteins to chitin surfaces (Bernard, M. P., et al. *Anal. Biochem.* 327:278-283 (2004); Ferrandon, S., et al. *Biochim. Biophys. Acta.* 1621: 31-40 (2003)). For example, the *B. circulans* chitinase A1 type 3 CBD has been used to immobilize fusion proteins expressed in bacteria on chitin beads to provide a platform for intein-mediated protein splicing (Ferrandon, S., et al., *Biochim. Biophys. Acta.* 1621: 31-40 (2003)) and to chitin-coated microtiter dishes (Bernard, M. P., et al., *Anal. Biochem.* 327:278-283 (2004)).

CBD as a component of chitinase can be obtained from many different sources, for example, fungi, bacteria, plants and insects. Any CBD originating from a chitinase may be used herein although CBDs separated from chitinase catalytic activity are preferred.

Nucleic acids encoding peptide building blocks (or fusion proteins) can be incorporated into bacterial, viral, insect, yeast or mammalian expression vectors so that they are operably linked to expression control sequences such as bacterial, viral, insect, yeast or mammalian promoters (or enhancers).

Nucleic acid molecules or expression cassette that encode peptide building blocks (or fusion proteins) may be introduced to a vector, e.g., a plasmid or viral vector, which optionally includes a selectable marker gene, and the vector introduced to a cell of interest, for example, a bacterial, yeast or mammalian host cell.

In one embodiment, the fusion polypeptides can be, for example, the peptide building blocks fused to an affinity tag polypeptide and a linker chitin binding domain (CBD) polypeptide. In these embodiments, the fusion polypeptide is expressed as a soluble complex. The affinity tag can be used to purify the fusion polypeptides by, for example, passing the culture lysates expressing the fusion polypeptide through an affinity chromatography column. The fusion polypeptides can bind to the column and can then later be eluted. Splicing of the fusion polypeptide at the linker can result in a composition that can include purified peptide building block. Methods of isolating truncated polypeptides using a recombinant expression system with fusion polypeptides are described, for example, in Cosert, K. M., et al. *Phys Chem Chem Phys* 19, 11163-11172, (2017), incorporated herein by reference in its entirety. Other expression system using other affinity tags may also be used and are within the scope of this description.

In one embodiment, the recombinant platform in the recombinant expression system can tag the pilin's N-terminus with a self-splicing intein linker and/or a solubility and affinity tag, e.g. Chitin Binding Domain or CBD. This system can facilitate the expression of the recombinant truncated PilA peptides in the soluble fraction collected from culture lysates and purification by affinity chromatography.

Examples of host cells useful for manufacture of peptide building blocks can include, but are not limited to, *E. coli, Salmonella* species, *Bacillus* species, *Streptomyces* species, and the like, plant cells, e.g. *Arabidopsis* species, *Taxus* species, *Catharanthus* species, *Nicotiana* species, *Oryza* species, soybeans, alfalfa, tomatoes, and the like), fungal cells (e.g., *Kluyveromyces* species, *Saccharomyces* species, *Pichia* species, *Hansenula* species, *Yarrowia* species, *Neurospora* species, *Aspergillus* species, *Penicillium* species, *Candida* species, *Schizosaccharomyces* species, *Cryptococcus* species, *Coprinus* species, *Ustilago* species, *Magnaporth* species, *Trichoderma* species, and the like), insect cells (e.g., Sf9 cells, Sf12 cells, *Trichoplusia* in cells, *Drosophila* species and the like), or mammalian cells (e.g., primary cell lines, HeLa cells, NSO cells, BHK cells, HEK-293 cells, PER-C6 cells, and the like). These cells may be grown in cultures ranging from microliter volumes to multiliter volumes.

In some embodiments, the peptide building blocks can include truncated PilA peptides. Truncated PilA peptides can be PilA peptides in which one or more amino acids are deleted. In one embodiment, the deletion of amino acids can be at the N-terminus end of the PilA peptides. Without being bound by any theory, it is understood that deletion of some or all of the hydrophobic region of the PilA peptide can increase the solubility of the peptide. In one embodiment, deletion of a portion of the N-terminal end can increase the solubility of the truncated PilA peptide while maintaining the ability of the truncated PilA polypeptide to form pilin nanowires that retain conductivity. In one embodiment, the ability to form nanowires and retain conductivity can be maintained by preserving the aromatic and charged residues found in the full-length native PilA peptide (SEQ ID NO:1).

In truncated PilA peptides, amino acids can be removed from the N-terminus or the C-terminus. In general, the N-terminus of nanowire peptides is more hydrophobic than the C-terminus, and the amino acids that participate in intramolecular and intermolecular electron transfer processes across and along the pilus nanowires are located closer to the C-terminus.

In some embodiments, one or more amino acids may be removed from the N-terminus of the pilin subunit. In other embodiments, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, or twenty two or more amino acids are removed from a nanowire peptide.

In some embodiments, the truncations may include step-wise codon reductions of the amino-terminus of the PilA peptides to reduce the subunit hydrophobicity and improve its expression in a heterologous host. The truncations generally do not affect amino acids shown to be involved in electron transfer and metal binding and are optimized to preserve the subunit ability to assemble via hydrophobic interactions.

In some embodiments, a string of amino acids can also be removed from nanowire peptides. For example, a sequential segment of about 1 to about 4 amino acids can be removed, or a sequential segment of about 1 to about 5 amino acids can be removed, or a sequential segment of about 1 to about 7 amino acids can be removed, or a sequential segment of about 1 to about 10 amino acids can be removed, or a sequential segment of about 1 to about 12 amino acids can be removed, or a sequential segment of about 1 to about 14 amino acids can be removed, or a sequential segment of about 1 to about 15 amino acids can be removed, or a sequential segment of about 1 to about 16 amino acids can be removed, or a sequential segment of about 1 to about 17 amino acids can be removed, or a sequential segment of about 1 to about 18 amino acids can be removed, or a sequential segment of about 1 to about 19 amino acids can be removed, or a sequential segment of about 1 to about 20 amino acids can be removed, or a sequential segment of about 1 to about 21 amino acids can be removed, or a sequential segment of about 1 to about 22 amino acids can be removed, or a sequential segment of about 1 to about 23 amino acids can be removed, or a sequential segment of about 1 to about 24 amino acids can be removed, or a sequential segment of about 1 to about 25 amino acids can be removed.

In one embodiment, the truncated PilA peptides can have a deletion within the first 22 amino acids of the PilA peptide. In some embodiments, truncated PilA peptides may have a truncation of about 10 to about 22 amino acids for solubility. In one embodiment, truncated PilA peptide can have a deletion of the first 10 amino acids ($PilA_{10}$). In one embodiment, truncated PilA peptide can have a deletion of the first 19 amino acids ($PilA_{19}$). In one embodiment, truncated PilA peptide can have a deletion of the first 20 amino acids ($PilA_{20}$). In one embodiment, truncated PilA peptide can have a deletion of the first 22 amino acids ($PilA_{22}$).

In some embodiments, the truncation may be within the hydrophobic region but may retain some of the terminal amino acids. For example, the truncated PilA peptides may have a truncation of from about amino acid 3 to about amino acid 20 of the PilA peptide, or from about amino acid 5 to about amino acid 20 of the PilA peptide, or from about amino acid 10 to about amino acid 22, further including any range therebetween. Other truncations are also possible and are within the scope of this description.

In one embodiment, this approach can recover PilA peptide building blocks in the soluble fraction of culture lysates fusion proteins containing pilins engineered with truncations of 10, 19, 20 and 22 amino acids as shown below.

```
PilA
                                          (SEQ ID NO: 1)
N-term- FTLIELLIVV AIIGILAAIA IPQFSAYRVK

AYNSAASSDL RNLKTALESA FADDQTYPPE S

PilA10
                                          (SEQ ID NO: 2)
N-term- AIIGILAAIA IPQFSAYRVK

AYNSAASSDL RNLKTALESA FADDQTYPPE S

PilA19
                                          (SEQ ID NO: 3)
N-term- AIPQFSAYRV KAYNSAASSD

LRNLKTALES AFADDQTYPP ES

PilA20
                                          (SEQ ID NO: 4)
N-term- IPQFSAYRVK AYNSAASSDL

RNLKTALESA FADDQTYPPE S

PilA22
                                          (SEQ ID NO: 5)
N-term- QFSAYRVKAY NSAASSDLRN

LKTALESAFA DDQTYPPES
```

FIG. 1B shows the alignment of pilA peptide (SEQ ID NO:1) aligned with $PilA_{10}$ (SEQ ID NO:2), $PilA_{19}$ (SEQ ID NO:3) $PilA_{20}$ (SEQ ID NO:4) and $PilA_{22}$ (SEQ ID NO:5).

In some embodiments, the conductive pili can have truncated pilin peptides with at least about 10%, or at least about 20%, or at least about 30%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, or at least about 97% sequence identity to a pilin peptide having an amino acid sequence comprising any of the SEQ ID NO:1-5.

In further embodiments, the truncated pilin peptides with at least 60% sequence identity of the SEQ ID NO:1 can have a truncation at the N-terminus of about 30 amino acids, or of about 1-28 amino acids, or of about 1-25 amino acids, or of about 1-22 amino acids, or of about 1-20 amino acids, or of about 1-19 amino acids, or of about 1-17 amino acids, or of about 1-15 amino acids, or of about 1-13 amino acids, or of about 1-12 amino acids, or of about 1-10 amino acids, or of about 1-9 amino acids, or of about 1-8 amino acids, or of about 1-7 amino acids, or of about 1-6 amino acids, or of about 1-5 amino acids, or of about 1-4 amino acids, or of about 1-3 amino acids, or of about 1-2 amino acids.

Chemical synthesis (to synthesize peptides de novo), chemical modification (e.g., which may include chemical stripping) or genetic engineering, can be used to manipulate the peptide composition, structure and binding properties of microbial nanowires to selectively modify conductance properties. Microbial nanowires can also be manipulated via genetic engineering to bind specific ligands for sensor design, controlled and specific deposition during device manufacturing, and the like. In one embodiment, genetic engineering or chemical modification is used to produce nanowires with various functionalities. In one embodiment, *Geobacter sulfurreducens*, is used. For additional details and sequence listings, see U.S. application Ser. No. 13/221,495, filed on Aug. 30, 2011 and entitled, "Microbial Nanowires," both of which are hereby incorporated by reference herein in their entireties.

In some embodiments, the peptide building blocks may be chemically synthesized and/or modified. Chemically modified peptide building blocks and polypeptides can be generated from nanowire peptides/polypeptides with a natural (non-recombinantly engineered) sequence that is chemically modified. In other embodiments, the chemically modified peptide building blocks can be generated with a mutant nanowire peptide that contains substitutions, deletions or additions of amino acids that are not normally found in naturally occurring pilus nanowires. Thus, for example, before chemical modification, the peptide building blocks can have a variant or modification thereof.

In some embodiments, the peptide building blocks can be chemically synthesized or modified after their synthesis to modulate the conductive, adhesive, coupling or other properties of the synthesized nanowires. The chemical modification may be performed on the peptide building block or after the synthesis on nanowires. Such chemical modification can be performed by procedures available in the art using a variety of reagents. For example, reagents such as performic acid, peroxides, iodoacetamide, iodoacetic acid, bissulfosuccinimidyl suberate (BS3), 1-ethyl-3-(3-dimethylaminopropyl) carbodiimide, N-ethylmaleimide, methyl methanethiosulfonate and S-(2,2,5,5-tetramethyl-2,5-dihydro-1H-pyrrol-3-yl)methyl methanesulfonothioate (MTSL) can be used to modify the conductive, adhesive, coupling or other properties of the nanowire polypeptides. In other embodiments, the nanowire peptides or polypeptides can be glycosylated, acylated or conjugated to an alkylene glycol (e.g., polyethylene glycol or PEG). Such modifications can be performed by procedures available in the art. See, e.g., John M. Walker, *The Protein Protocols Handbook* (2002); Means, G. E. and Feeney, R. E. *Chemical Modifications of Proteins*. Holden-Day, San Francisco (1971).

In one embodiment, the $PilA_{19}$ can be used as a peptide building block in a method for the synthesis of protein nanowires. In one embodiment, peptide building blocks that can be solubilized in a buffer may be used as peptide building blocks in the synthesis of protein nanowires. The description herein discloses the synthesis of protein nanowires with $PilA_{19}$ as the peptide building block. It will be understood that other peptide building blocks such as other truncated PilA peptides may also be used, and all are within the scope of this description.

In one embodiment, the truncated PilA peptides can be separated from other proteins in a chitin column as shown in FIG. 2. Truncated Pil A peptides with 10, 19, 20 and 22 amino acids removed from the N-terminus will be referred to herein as $PilA_{10}$, $PilA_{19}$, $PilA_{20}$ and $PilA_{22}$, respectively.

In one embodiment, truncating 19 amino acids ($PilA_{19}$) can reverse the sign of the grand average hydropathy (GRAVY) score of the $PilA_{19}$ peptide from (+0.51) to (−0.55). This can be indicative of the solubility of the truncated peptides and can permit the high-yield recovery of the truncated PilA peptides, e.g. $PilA_{19}$ peptide, after cleavage from the CBD tag as shown in FIG. 2. In one embodiment, the cleavage efficiency can be highest for $PilA_{19}$ than for other soluble peptides such as $PilA_{20}$ and $PilA_{22}$. This can allow for the nearly complete recovery of the peptide after cleavage for 24 h at room temperature as shown in FIG. 2. This can be due to the fusion of the 19 amino acid truncation peptide to the intein linker via a residue (alanine as shown in FIG. 1) that can be optimal for DTT-induced cleavage.

The peptide building blocks can be purified by any available method. In one embodiment, the method includes lysis of cells expressing the peptide building blocks, followed by selective removal of contaminating cell macromolecules, and then selective separation of pure peptide building blocks from other proteins. In one embodiment, a single step purification method is used which may have yields in excess of 50%, such as up to 55% or up to 60% or higher, including any and all ranges there between. In one embodiment, the yield is at least about 63%. Higher yields, in excess of 63% may also be possible, such as up to about 95%, including any and all ranges there between. The protocol is flexible, in the sense that it can be adapted for use with substantially any sample of peptide building block expressing cells, substantially any method to remove contaminating cell macromolecules that do not affect the integrity of the peptide building blocks, and substantially any method to selectively separate the peptide building blocks from other contaminating proteins.

In some embodiments, the host cells are used to mass-produce the peptide building blocks and then purified for self-assembly of the nanowires or pili as described herein. In some embodiments, the fusion partner peptide is a chitin binding domain. When the fusion partner peptide is a chitin binding domain, a matrix or solid substrate containing a carbohydrate can be used, where the carbohydrate is bound by the chitin binding domain. For example, the chitin binding domain(s) can bind chitin. Chitin can be linked, adsorbed or covalently bound to a solid substrate such as a bead, column matrix or a coated surface. The solid substrate may, for example, magnetic chitin beads, colloidal chitin or environmental chitin. The chitin may also be immobilized in a column or coated on a solid surface. In one example, sterile chitin beads are added directly to culture medium so that protein production and harvesting can occur simultaneously during the fermentation process (see, e.g., U.S. Pat. No. 7,732,565 or U.S. Patent Application Publication. No. 2006/041849, both of which are hereby incorporated by reference herein in their entireties).

Once the solid substrate (e.g., beads, matrix or a column) has been washed to remove contaminating molecules, the peptide building blocks can be obtained by cleaving a bond linking the nanowire peptide to the fusion partner peptide, then washing the peptide from the solid substrate, leaving the fusion partner peptide attached to the solid substrate. It may be desirable to elute the peptide building blocks from the matrix under non-denaturing conditions.

For example, a fusion protein that includes a fusion partner peptide that binds to a binding entity can he affinity purified by contacting the fusion protein with a solid substrate to which the binding entity is absorbed or bound, After binding to the fusion protein to a solid substrate, the fusion partner peptide can be cleaved, and the peptide building blocks can be washed from the solid substrate. The fusion partner peptide can be retained by the solid substrate. For example, the peptide building blocks can be cleaved from a CBD fusion partner peptide by washing the solid substrate with a reducing agent such as β-inercaptoethanol or dithiothreitol.

Figure 3:
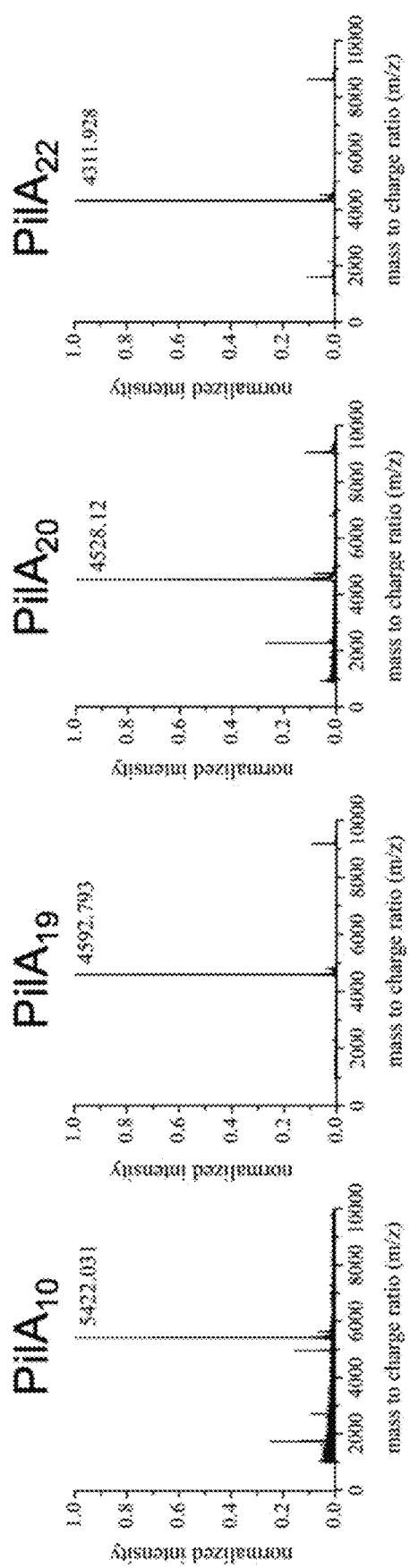
FIG. 3 is a plot of MALDI-TOF MS analysis of PilAn peptides eluted from chitin column after cleavage with DTT for 24 h at 23° C. The theoretical molecular mass of the truncated pilins is: 5,431 Da ($PilA_{10}$), 4,595 Da ($PilA_{19}$), 4,524 Da ($PilA_{20}$), and 4,314 Da ($PilA_{22}$).

In some embodiments, the expression of the recombinant fusion proteins, e.g. pilA peptide-CBD, can be similar with all the truncated pilins. In some embodiments, the amount of peptide that can be eluted from the column after DTT cleavage of the CBD can vary widely as shown in FIG. 2. In one embodiment, the cleavage efficiency via intein self-splicing can be sensitive to the peptide residues adjacent to the intein linker and the temperature during the elution from the column. In one embodiment, increasing the temperature from about 4° C. to about 23° C., for example, can improve the cleavage efficiency for all the $PilA_n$ peptides. In one embodiment, increasing the temperature can also promote the aggregation of the hydrophobic peptide, e.g. $PilA_{10}$ after cleavage. As a result, yields of $PilA_{10}$ in solution can be too low to detect the peptide band in an SDS-PAGE gel. In one embodiment, low yields of $PilA_n$, such as $PilA_{10}$, can be detected by MALDI-TOF mass spectrometry as shown in FIG. 3.

Figures 4A, 4B, 4C:
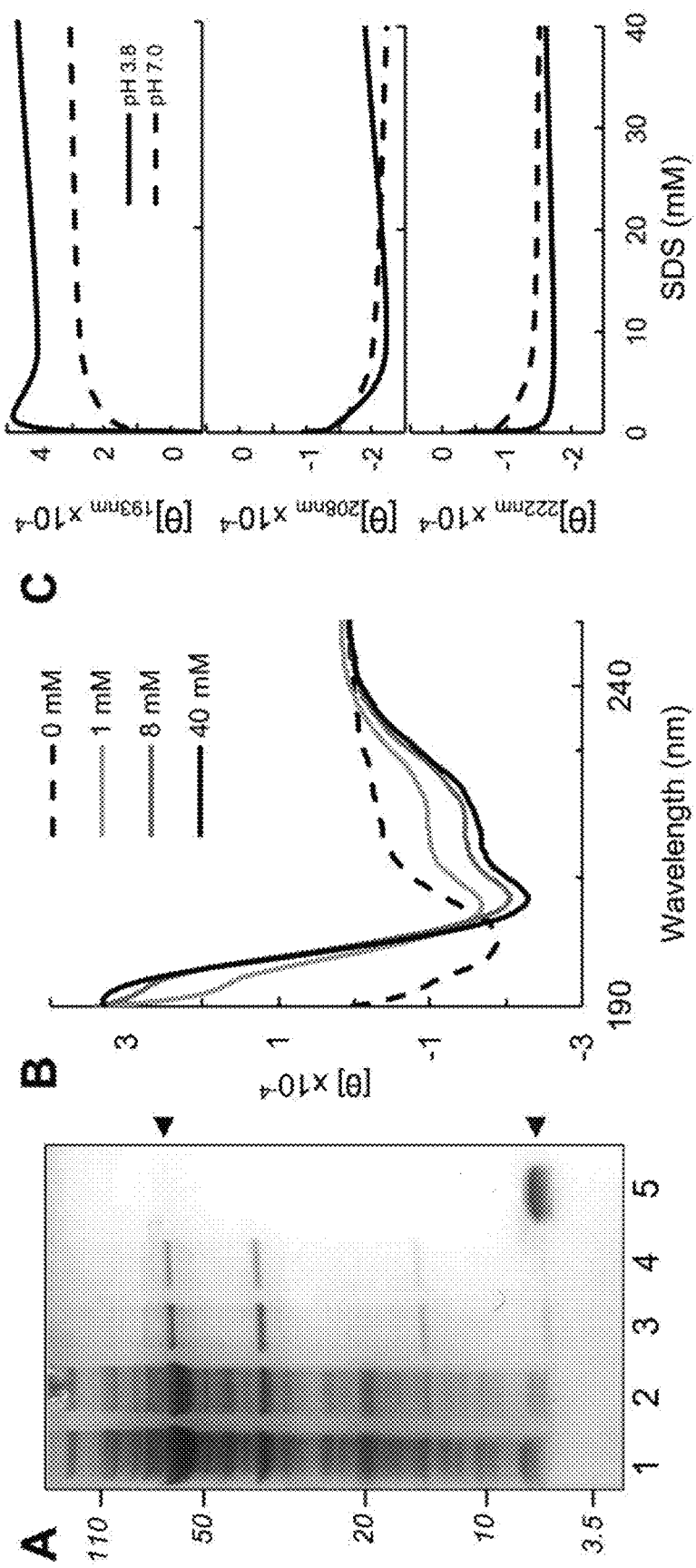
FIG. 4A is a photograph of SDS-PAGE gel showing the enrichment of the CBD-$PilA_{19}$ fusion protein (black arrow) in the soluble (lanes 1-2) rather than insoluble (lane 3-4) proteins from two independent culture lysates. Lane 5 shows the migration of the recombinant $PilA_{19}$ peptide (red arrow) eluted from the chitin column after DTT-induced cleavage from the CBD domain. Numbers at right are molecular weight standards in kDa.
FIG. 4B is a plot of the effect of SDS detergent on $PilA_{19}$ helicity by Circular Dichroism (CD). The plot shows the CD spectra collected at increasing concentrations of SDS at pH 7.
FIG. 4C is a plot of the effect of pH on molar ellipticities at key wavelengths in the CD spectra for pH 3.8 and pH 7.

In one embodiment shown in FIG. 4A, a recombinant production cycle of $PilA_{19}$ building blocks is shown with the enrichment of the CBD-$PilA_{19}$ fusion protein in soluble fractions collected from replicate culture lysates and the purification of the $PilA_{19}$ peptide after incubating the chitin-bound CBD $PilA_{19}$ protein with DTT at room temperature (23° C.) for 24 h.

In one embodiment, the peptide building blocks can be evaluated with respect to the secondary structure and folding dynamics. A variety of methods can be used to evaluate the secondary structure of the peptide building blocks and all are within the scope of this description.

In one embodiment, circular dichroism (CD) can be used to investigate the secondary structure and folding dynamics of $PilA_{19}$. (FIG. 4B). In one embodiment, maintaining a helical conformation can be advantageous for pilin peptides to establish hydrophobic interactions during fiber formation. In one embodiment, a detergent such as sodium dodecyl sulfate (SDS) can be used to determine the formation of α-helical conformations of a truncated pilin polypeptide and suitability for fiber formation. In one embodiment, the ellipticity of a truncated polypeptide may be measured to determine the formation of an ordered structure such as an α-helix.

In one embodiment, the methods described herein can include in vitro self-assembly of the peptide building blocks to produce filaments analogous to the native ones that have customizable structural and functional properties. In some embodiments, genetic engineering can also be used to add functional groups to the peptide building blocks, (e.g., for enhancing manufacture, folding, assembly, binding and other useful properties (e.g., including allowing synthesis of functionalized nanowires in nanostructured interfaces).

In one embodiment, only one type of purified peptide building block can be provided during self-assembly for formation of recombinant nanowires. In one embodiment, a mixture of two or more purified peptide building blocks can be provided during self-assembly for formation of recombinant nanowires. In one embodiment, different peptide building blocks can be provided simultaneously or separately at the initial assembly reaction or during refeeding of the assembly components as described below during synthesis of nanowires.

In one embodiment, the method further includes suspending the purified peptide building blocks, e.g. truncated pilin peptides, in an assembly buffer. Assembly buffer can be any solvent or combination of solvents that can maintain the peptide building blocks in solution and/or the peptide structure and/or charge that is optimal for nanowire formation. In one embodiment, the assembly buffer can include a solvent that is less than polar than water. In one embodiment, the assembly buffer can include a solvent that stabilizes the peptide's helical structure. Assembly buffer can include, for example, acetonitrile, methanol or a combination of the two. Other solvents may also be used and are within the scope of this description.

In one embodiment, the assembly buffer can include a combination of solvents. In one embodiment, the assembly buffer can include an organic solvent such as acetonitrile that can maintain the peptide building blocks in solution. In one embodiment, the assembly buffer can include other solvents, such as methanol, that can stabilize helical peptide conformations. Other solvents that stabilize helical peptide conformations can include, for example, trifluoroethanol.

In one embodiment, the assembly buffer can include acetonitrile and methanol. In one embodiment, the assembly buffer can be an acetonitrile:methanol having a ratio of about 90:10, or about 80:20, or about 70:30, or about 60:40, or about 50:50, or about 40:60, or about 30:70, or about 20:80, or about 10:90. Other combinations of solvents may be used that can maintain the peptide building blocks in solution. In one embodiment, the assembly buffer can be acetonitrile:methanol having a ratio of about 80:20.

In some embodiments, assembly buffer may comprises an aqueous solution of methanol or trifluoroethanol. In one embodiment, assembly buffers with chemically synthesized peptides may include solvents with water.

The concentration of the peptide building blocks in the assembly buffer can vary. In one embodiment, the concentration of the peptide building blocks in the assembly buffer is at least about 3 mg/ml. In one embodiment, the concentration of the peptide building blocks in the assembly buffer is from about 3 mg/ml to about 15 mg/ml. In one embodiment, the concentration of the peptide building blocks in the assembly buffer is from about 7 mg/ml to about 10 mg/ml.

In one embodiment, the method can include initiating nucleation of peptide building blocks to self-assemble and promote the self-assembly of the peptide building blocks in the assembly buffer to form fibers. The method can include providing a hydrophobe in the assembly buffer to form an assembly composition. In one embodiment, the assembly composition can include the peptide building blocks and a hydrophobe in the assembly buffer. Hydrophobes can be molecules and/or materials that can serve as the nucleating site and can guide self-assembly of peptide building blocks into protein fibers.

In one embodiment, the hydrophobe can include long chain carbon molecules. In one embodiment, the hydrophobe can include long chain carbon non-polar molecules. In one embodiment, the hydrophobe can include at least about 8 carbons, or at least about 10 carbons, or at least about 13 carbons, or at least about 15 carbons, or at least about 17 carbons, or at least about 18 carbons, or at least about 20 carbons in the carbon molecules.

In one embodiment, the hydrophobe can be a hydrophobic chemical molecule. In one embodiment, the hydrophobe can be an alkane. In one embodiment, the hydrophobe can be chemical molecules, such as a detergent, dextran, methacrylate and the like, added directly to the solvent or in surface constrained forms such as coatings on silica or agarose beads. In one embodiment, the hydrophobe is octadecane.

In one embodiment, the hydrophobe can be added to the assembly buffer with the peptide building blocks. The amount of the hydrophobe that can be included can vary and may be dependent on the amount and type of the peptide building blocks. In one embodiment, the ratio of hydrophobe to peptide building block is at least about 1:20. In one embodiment, the ratio of hydrophobe to peptide building block is from about 1:20 to about 1:500, or from about 1:50 to about 1:200, or from about 1:80 to about 1:120. In one embodiment, the ratio of hydrophobe to peptide building block is about 1:100.

In one embodiment, an optimal concentration of the peptide may be established first. Then the concentration of the peptide can be kept constant to calculate the concentrations of hydrophobe that can promote fiber formation.

In one embodiment, the method of providing a hydrophobe can include the use of a column to perform a buffer exchange by transferring the peptide building blocks from an elution buffer to an assembly buffer. In one embodiment, elution buffer can elute the peptide from the chitin column after DTT-induced splicing from the CBD-intein module.

In one embodiment, the buffer exchange can lead to the co-elution of the peptide building blocks with a hydrophobe into the assembly buffer. In one embodiment, the buffer exchange column can include particles coated with long chain carbon molecules.

In one embodiment, the hydrophobe can be a material such as particles coated with long chain carbon molecules. These particles can be the particles in the buffer exchange column. The long chain carbon molecules can be non-polar carbon molecules. In one embodiment, the hydrophobe can include, for example, silica particles. Other particles can function as hydrophobes such as for example, agarose, which is used extensively to make hydrophobic resins such as Superdex® (dextran cross-linked with agarose beads). In some embodiment, particles made with hydrophobic epoxy resins may also be included as a hydrophobe. In one embodiment, the silica particles can be coated with long chain carbon molecules. In one embodiment, the hydrophobe can be octadecyl-silica particles. Other materials that can be used to make beads of the desired size and coated with a hydrophobic ligand such as an alkane. Beads can be, for example, from about 0.25 um to about 2 um. In one embodiment, the beads can be from about 0.5 um to about 1 um.

In one embodiment, the buffer exchange column can be a reverse phase column. In one embodiment, the reverse phase column can include silica particles. In one embodiment, the reverse phase column can include octadecyl-silica particles.

In one embodiment, the method can include loading a buffer exchange column with peptide building blocks. In one embodiment, the peptide building blocks can be in an elution buffer. In one embodiment, the peptide building blocks can be soluble in the elution buffer after cleavage of the affinity tag from the recombinant host system. In other words, the elution buffer can be a buffer that can maintain the purified peptide building blocks in solution.

In one embodiment, after loading the peptide building blocks for the buffer exchange, the column can be washed with water or a resin-compatible buffer. The washing can remove the impurities. The assembly buffer can be added to detach the peptide from the resin for collection in a tube. In one embodiment, the column may be washed with about 5 ml of liquid, or from about 5 ml to about 10 ml of liquid, or from about 10 ml to about 15 ml of liquid, or from about 15 ml to about 20 ml of liquid, or from about 20 ml to about 25 ml of liquid, or from about 25 ml to about 30 ml of liquid. The liquid for washing the column can be a buffer, water and the like.

In one embodiment, a buffer exchange may be conducted to transfer the peptide building blocks from the elution buffer (from the chitin column) to the assembly buffer. In one embodiment, after the peptide building blocks are loaded onto the buffer exchange column, the peptide building blocks can be eluted into the assembly buffer.

In one embodiment, the peptide building blocks can be loaded onto the column in elution buffer (from the chitin column). The peptide building blocks are retained in the column and the elution buffer may be washed away using other buffers or water. The buffer exchange column with the bound peptide blocks can be washed with water. Assembly buffer can then be added to the column to detach the peptide building blocks. Thus, the peptide building blocks go into the column in elution buffer and come out in assembly buffer resulting in a buffer exchange.

In one embodiment, the elution of the peptide building blocks can also lead to co-elution of the buffer exchange column particles into the assembly buffer. In one embodiment, the coated particles from the buffer exchange column can serve as the hydrophobe in the assembly composition. In one embodiment, the loading of the column, washing and elution can be performed using a gravity flow rate.

In one embodiment, the pH of the peptide building block composition at the time of loading is about 9 and after elution is about neutral. The pH of the composition at the time of loading and elution can vary. Other pH's at the time of loading and elution are also within the scope of this description.

The concentration of the peptide building blocks in the assembly buffer after elution can vary. In one embodiment, the concentration of the peptide building blocks in the assembly buffer after elution can be from about 1 mg peptide/ml to about 8 mg/ml. In one embodiment, the concentration of the peptide building blocks in the assembly buffer after elution can be from about 2 mg peptide/ml to about 5 mg peptide/ml. In one embodiment, the concentration of the peptide building blocks in the assembly buffer after elution can be about 3 mg peptide/ml.

The amount of the coated column particles in the assembly composition can vary. In one embodiment, the amount of coated column particles can be from about 1 mM to about 10 mM in the assembly composition. In one embodiment, the amount of coated column particles can be from about 2 mM to about 5 mM in the assembly composition. In one embodiment, the amount of coated column particles can be from about 3 mM to about 4 mM in the assembly composition. In one embodiment, the amount of coated column particles can be about 3.5 mM in the assembly composition.

In one embodiment, the method can further include evaporating the assembly buffer in the assembly composition after the addition of a hyrophobe. In one embodiment, the assembly composition may be formed by the addition of a hydrophobe to the assembly buffer containing the peptide building blocks. In one embodiment, the assembly composition may be formed by co-elution of the hydrophobe with the peptide building blocks. Evaporation of the assembly buffer from the assembly composition can increase the molecular crowding in the assembly composition. Without being bound by any theory, it is believed that increase in molecular crowding can create a hydrophobic environment that can promote peptide-peptide interactions and lead to assembly of the pilin peptides into fibers.

A variety of methods can be used to promote evaporation of the assembly buffer. In one embodiment, the evaporation of the assembly buffer can be performed by a SpeedVac Concentrator. In one embodiment, evaporation of the assembly buffer can occur by centrifugation of the tube with the assembly composition. This can be conducted with the tube open, e.g. not sealed, so that evaporation of the assembly buffer can occur. An exemplary method of evaporation is described below in the Examples. It will be understood other methods are known in the art and may be used to promote evaporation of the liquid from the assembly composition.

In one embodiment, a portion of the assembly buffer can evaporate from the assembly composition. In one embodiment, all of the assembly buffer can evaporate from the assembly composition. In one embodiment, at least about 25% of the assembly buffer may evaporate, or at least about 50% of the assembly buffer may evaporate, or at least about 75% of the assembly buffer may evaporate, or at least about 85% of the assembly buffer may evaporate, or at least about 90% of the assembly buffer may evaporate, or at least about 95% of the assembly buffer may evaporate.

In one embodiment, the method can include performing one or more elongation cycles. In one embodiment, an elongation cycle can include refeeding the assembly composition with additional peptide building blocks after evaporation, mixing the assembly composition after refeeding and evaporating the liquid in the assembly composition.

In one embodiment, the method can include two or more elongation cycles. In one embodiment, the method can include three or more elongation cycles. In one embodiment, the method can include from about 3 elongation cycles to about 6 elongation cycles. In one embodiment, the method can include from about 3 elongation cycles to about 5 elongation cycles. In one embodiment, the method can include about 4 elongation cycles.

In one embodiment, the elongation cycle can include refeeding the assembly composition with additional peptide building blocks. In one embodiment, refeeding may include addition of hydrophobe and/or additional assembly buffer to the assembly composition. Refeeding can provide additional building blocks for generating fibers and/or nanowires. It can also increase molecular crowding to further promote fibers and/or nanowires.

In one embodiment, the same peptide building blocks can be added during each refeeding step. In one embodiment, different peptide building blocks may be added during the refeeding step. In one embodiment, peptide building blocks can include a mixture of different peptide building blocks. In one embodiment the peptide building block mixture can include 2, or 3, or 4, or 5 or more, or 10 or more, or 15 or more different peptides in the peptide building block mix. In one embodiment, the same peptide building block mixture can be added during each refeeding step. In one embodiment, different peptide building block mixture can be added during each refeeding step.

In one embodiment, the method can further include mixing the composition after the refeeding with peptide building blocks and assembly buffer. Mixing can resuspend the peptides and/or fibers already formed and can increase the interaction between the newly added peptide building blocks and the peptides and/or fibers already present in the assembly composition. This can allow the interaction and incorporation of the newly added peptide building blocks with peptides and/or fibers already present in the assembly composition to further elongate and/or widen the peptides and/or fibers.

In one embodiment, mixing can be done by aspirating the assembly composition in and out of a micropipette multiple times to disperse the components in the assembly composition. In one embodiment, the tube or vessel with the assembly composition can be vortexed to disperse the components in the assembly composition. In one exemplary embodiment, mixing may be performed as described in the Examples below or any type of mechanical agitation. Other methods for mixing the components are known in the art may also be used and all are within the scope of this description.

In one embodiment, the method can include harvesting the synthesized nanowires by processing after the last elongation cycle. The processing steps can include, for example, drying the synthesized nanowire composition, resuspending the nanowire composition, precipitating the nanowire composition, and/or lyopholization may be performed. In one embodiment, precipitation of the fibers by acetone may be performed to remove the silica beads. In one embodiment, nanowires formed in the assembly composition can be dried after the last elongation cycle has occurred. The dried assembly composition can be resuspended in a liquid such as water or buffer. In one embodiment, the nanowires may be precipitated by acetone, o/n and recovered by centrifugation. In one embodiment, the nanowires can be dried under a stream of N2 and stored for further use.

Figure 11:
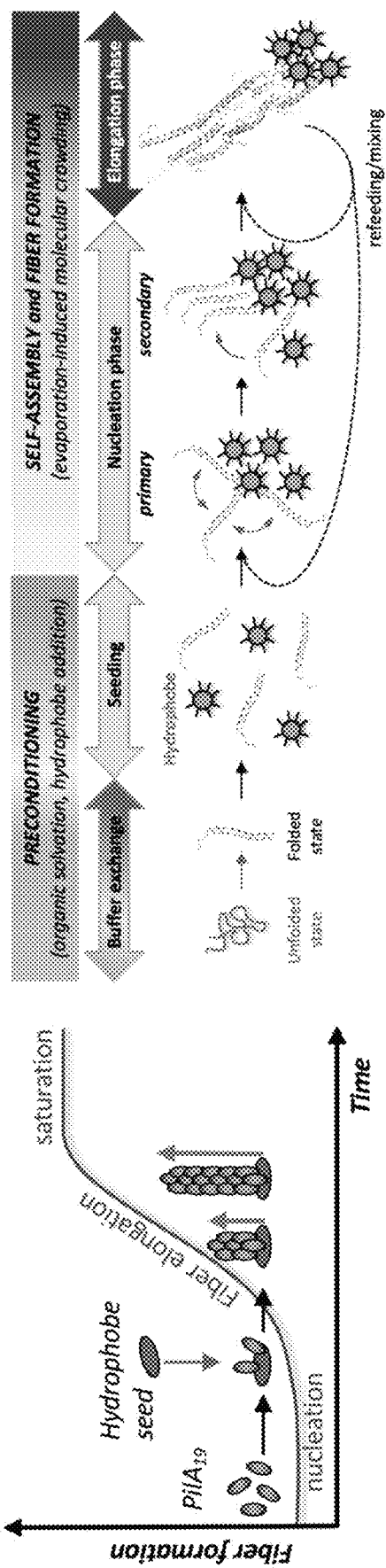
FIG. 11 is a schematic diagram of steps and model of PilA$_{19}$ fiber formation. (Left) Steps in the bottom-up fabrication of protein nanowires with PilA$_{19}$ peptide building blocks triggered in the presence of a hydrophobe. (Right) Nucleation-dependent polymerization model of hydrophobe-triggered pilin assembly showing the three phases of nucleation, fiber elongation, and saturation.

In one embodiment, FIG. 11 shows a schematic diagram of the polymerization of peptide building blocks to form recombinant nanowires. The pilins polymerized in vitro can follow kinetics that fit the typical nucleation-dependent polymerization model. Nucleation-controlled aggregation kinetics can include an initial lag phase of molecular organization and peptide nucleation that can be accelerated in the presence of seed molecules such as hydrophobes. A linear phase of fiber growth then follows until reaching a saturation or stationary phase, which marks the equilibrium between soluble monomers and fibers and the end of fiber growth. As shown in FIG. 11, the lag phase can be minimized by suspending the peptide building block monomers in an organic solvent that stabilized the peptide's helical conformation and adding a hydrophobe that provided seed molecules to trigger nucleation and guide fiber growth. The controlled evaporation of the solvent can increase molecular crowding and promote the initial nucleation of the pilins on the seed or hydrophobe molecules (primary nucleation) and their spontaneous self-assembly as short fibers (secondary nucleation). Fiber elongation depended on the availability of hydrophobe and peptide building blocks supplied in subsequent refeeding steps but also on reaction mixing, which increased the number of nucleation sites and the incorporation of monomers into the growing fibers until reaching the saturation phase.

Octadecane, whether in solution (FIG. 9A-9B) or immobilized on silica particles (FIG. 5A), can be a suitable hydrophobe to trigger pilin nucleation and fiber formation. This can suggest that the hydrophobe does not need to be incorporated into the fiber but, rather, it provides a physical site to nucleate the pilins and guide their self-assembly as fibers (FIG. 11). The addition of the hydrophobe in a surface-constrained form can also permit its separation from the fibers by centrifugation at the end of the assembly reaction. The emission of silica from nanosized particles in a precise region of the UV spectrum (FIG. 6A) also proved useful to optimize the concentration of hydrophobe.

Figures 5A, 5B, 5C:
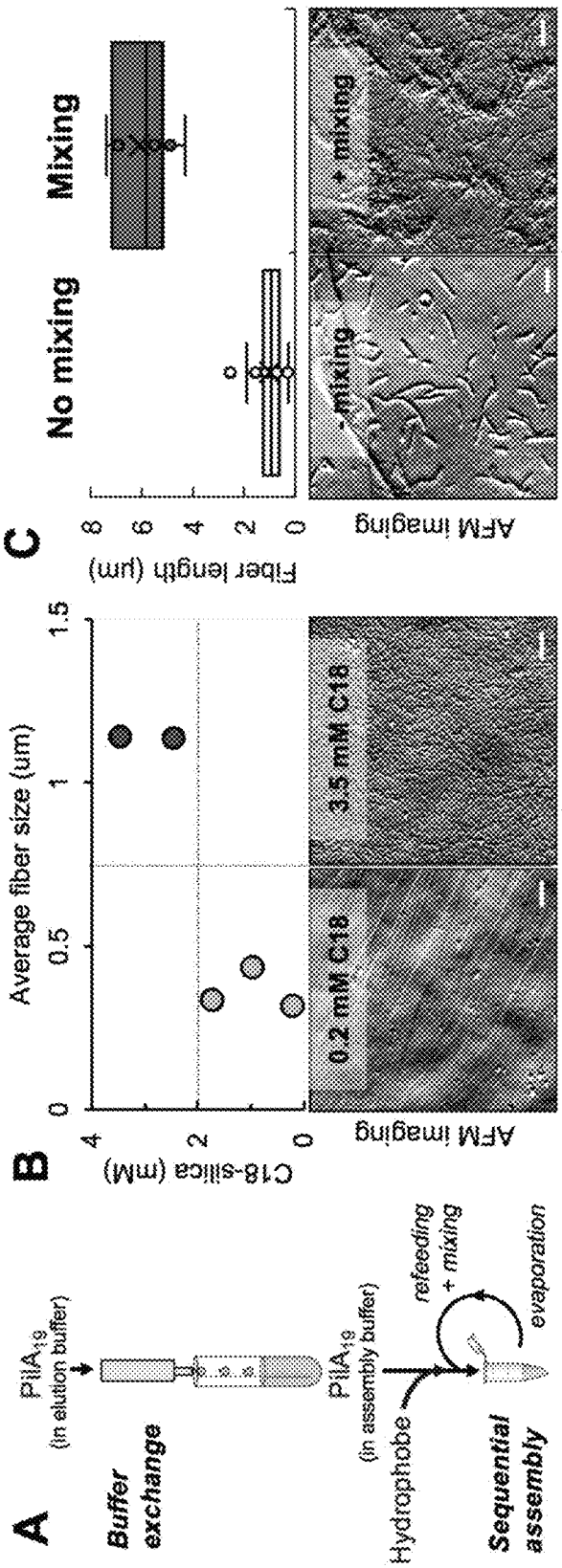
FIG. 5A is a schematic diagram of evaporation-induced self-assembly of recombinant $PilA_{19}$ peptides. The protocol illustrates the key steps in the assembly of $PilA_{19}$ fibers. The evaporation-induced assembly included sequential additions of the peptide solution to elongate the fibers.
FIG. 5B is a plot (top) and an image (bottom) showing the hydrophobe (C18-silica particles) dose effect on fiber formation, estimated as average fiber size by dynamic light scattering (plot, on top) and AFM imaging on HOPG (bottom; images are for 0.2 or 3.5 mM C18-silica reaction mixes only).
FIG. 5C is a plot (top) and an image (bottom) showing the effect of reaction mixing on fiber elongation (box plot). Boxes in plot contain 50% of all values and whiskers represent the 25th and 75th percentiles of fiber lengths measured by analyzing AFM images of random fields with samples (bottom) with the ImageJ software. The median is shown as a horizontal line across the boxes, average as a cross, and outliers as circles outside the boxes. Scale bar in the AFM images in FIGS. 5B and 5C is 1 μm.

In one embodiment, at optimal hydrophobe concentrations, and with sufficient peptide refeeding and reaction mixing steps, $PilA_{19}$ fibers were synthesized approximately 6-μm long that dispersed well in mild aqueous solutions (FIG. 5A-5C). This contrasts with purification protocols available for native pili, whose longer and heterogeneous length promotes the formation of large supramolecular structures that are difficult to disrupt without denaturing the pilus fiber core (FIG. 5A). The reduced aggregation of the $PilA_{19}$ fibers can also facilitate their deposition on electrode surfaces and electronic characterization by scanning probe methods (FIG. 10A-10H).

In one embodiment, the nanowires synthesized according to the methods described herein can be produced in large quantities using a simple protocol relative to the natural nanowires.

In one embodiment, nanowires having a length of at least about 1 μm can be generated. In one embodiment, nanowires having a length from about 4 μm to about 10 μm can be generated. In one embodiment, nanowires having a length from about 5 μm to about 7 μm can be generated.

In one embodiment, synthesized nanowires having an average diameter of at least 1 nm can be generated. In one embodiment, synthesized nanowires having an average diameter of from about 1 nm to about 3 nm can be generated. In one embodiment, synthesized nanowires having an average diameter of about 2 nm can be generated.

In one embodiment, the synthesized fibers and nanowires can be characterized by a variety of methods and techniques.

In one embodiment, the fibers can be characterized by performing circular dichroism (CD) spectra on a sample of the fibers and/or nanowires. The ratio of the intensity at 222 nm and 208 nm can be used to indicate the helical content of the sample. In one embodiment, the ratio of 222 nm/208 nm is from about 0.7 to about 0.9. In one embodiment, the ratio of 222 nm/208 nm is from about 0.9 to about 2 or higher.

In one embodiment, the nanowires can be characterized by performing scanning probe microscopy. In one embodiment, the fibers or nanowires can be deposited on the surface of Highly Oriented Pyrolytic Graphite (HOPG) as described in the Examples below. In one embodiment, the nanowires can have rectifying behavior. In one embodiment, analyses of the asymmetry of the IV plots can have a rectification score below about 1.

In one embodiment, the nanowires can be chemically fixed prior to use in devices as described herein.

In one embodiment, the synthesized nanowires can transfer electrons to metal cations. The nanowires can transfer electrons to a variety of ions including, for example, Fe(III), uranyl cation and the like.

The nanowire proteins synthesized by assembly of modified PilA peptides can be essentially pure. Synthesized nanowires can be free of contaminants, metals, ions, metalloenzymes, flavins, quinones and other redox cofactors that can be found in purified, naturally occurring nanowires. In one embodiment, the synthesized nanowires can be composed of truncated PilA peptides that polymerize according to the methods described herein via hydrophobic interactions to form the pilus, i.e., synthesized nanowire filament. These nanowires can be stored dry substantially indefinitely and can be resuspended in appropriate solvents, as needed, for downstream applications. As noted herein, these novel synthesized nanowires have conductive (e.g., rectifying) behavior due, in part, to the polarized nature of proteins, containing an N-terminus (positively charged) and a C-terminus (negatively charged) end. Particular rectifying behavior can also be due to the protein composition (i.e., amino acid make-up) and structure of the nanowire (i.e., due to the alignment of dipoles of peptide bonds in the pilin's α-helix).

The nanowire polypeptides described herein can have asymmetrical conducting properties due to the protein composition (i.e., amino acid make-up) and structure of the nanowire. Such conducting activity can also be characteristic of the disclosed nanowire peptides and polypeptides in pure form, for example, in absence of metals and cellular contaminants that could mask the natural rectifying properties of the nanowire.

By combining more than one asymmetric conductor together, a device can be made with a variety of conductive properties. Moreover, the conductive properties of such a device can be altered by employing genetically or chemically modified nanowire peptides and or by incorporating other materials available to those of skill in the art.

Devices that include microbial nanowires are desirable because the nanowire peptides can be mass-produced and induced to self-assemble to produce the nanowires. This can enable the mass-production of nanowire-containing devices at a low cost.

The disclosed synthesized nanowires may be used in various device applications such as antenna, attenuator, battery, brush, capacitor, condenser, conductor, circuit, electrode, fuel cell, generator, filter circuit breaker (fuse), inductor, coil, nanowire array, particle collector, precipitator, reactor, rectifier, relay, resistor, solar energy collector, spark generator, suppressor, terminal, and the like.

The synthesized nanowires can also be used, for example, for construction of active devices such as transistors. With regard to nano-electronics, the conductive behavior of nanowires means that protein-based diodes (one-way conductors) can be constructed from these nanowires. In conventional microelectronics, diodes are the basic building blocks for transistors and more complex active components, including the microprocessors that run our computers. Hence, the conducting behavior of the nanowires opens the door to the construction of protein-based nano-electronics transistors and more complex devices.

In one embodiment, nano-electronics include, for example, radio demodulation (rectification of AM radio frequency signals to make audio signals), low voltage AC-DC power conversion, current steering, power switches and over-voltage protection. Other embodiments include, but are not limited to, the logic circuitry in electronic devices such as laptop computers, cellular phones and similar devices, further including computer chips, such as those used in the transportation industry, such as in aircraft and automobiles.

In some embodiments, the nanowire polypeptides can be configured to include branches, for example, by chemically linking two or more nanowire peptides or polypeptides together. Thus, the nanowire polypeptides can be assembled into a main pilus that is elongated and has a selected or desirable length. A plurality of branch pili may emanate from the main nanowire pilus at one or more substantially fixed distances along the length of the main pilus. The main pilus may also include one or more junctions with one or more secondary main pili, where the junctions are substantially perpendicular to the length of the main pilus. In some embodiments, junctions may be developed by growing or expressing nanowire peptides between two regions that may be electrically connected.

In another embodiment, the nanowire peptides can be configured to form part of an apparatus. For example, the apparatus may contain at least one pilus having truncated nanowires peptides. In other embodiments, the apparatus may contain at least one junction between pili. For example, the apparatus may include a plurality of junctions. Each junction may include a branch pilus and an elongate main pilus. For example, each junction may be situated at an interface between a branch pilus and the elongate main pilus.

In one embodiment, the disclosed pili are used in the design and fabrication of biobased devices. Such devices may include biosensors, biocatalytic systems, biofuel cells, and heavy-metal transformation systems and the like. In some embodiments the pilin monomers or pili may be interfaced with a suitable substrate such as gold or carbon. Substrates suitable for fabricating bioelectronic interfaces include substrates that allow nanowires to self-assemble and be conductive.

In some embodiments, the synthesized nanowires can be used to bind and reductively precipitate toxic contaminants such as uranium along the nanowires.

Embodiments of the invention will be further described by reference to the following examples, which are offered to further illustrate various embodiments of the present invention. It should be understood, however, that many variations and modifications may be made while remaining within the scope of the present invention.

EXAMPLES

Materials and Methods

Bacterial strains and culture conditions. *Geobacter sulfurreducens* strain PCA was routinely grown in anaerobic NB medium with 20 mM acetate as electron donor and 40 mM fumarate as electron acceptor. Genomic DNA extracted from these cultures was used as template to PCR-amplify the native pilA gene (GSU1496) and engineer recombinant pilin production systems in *E. coli* Rosetta™ 2 (DE3) pLysS cells (Novagen), as described below. The *E. coli* cultures were propagated in Luria Bertani (LB) medium supplemented with antibiotics, as described below, and preserved in 20% glycerol at −80° C.

Design, recombinant production and purification of truncated pilins. The truncated pilins used in this study (PilA$_{10}$, (SEQ ID NO:2); PilA$_{19}$, (SEQ ID NO:3); PilA$_{20}$, (SEQ ID NO:4); and PilA$_{22}$, (SEQ ID NO:5)) are derivatives of the mature PilA peptide of *G. sulfurreducens* carrying 10, 19, 20 and 22 amino acid truncations at the peptide's N-t. The truncation design was based on analyses of the hydrophobic regions and aggregation potential of the PilA peptide (i.e., the pilin without its signal peptide) based on computational predictions with AGGRESCAN, grand average hydropathy (GRAVY) scoring, and Kyte Doolittle test. All truncations preserved the aromatic and charged amino acids of the pilin that are critical for conductivity and formation of salt bridges. Pilin design also involved computational analyses of MD-optimized structural models of the PilA pilus fiber (GPIL-WT.pdb) and PilA pilin (pilin-WT.pdb) constructed with the MacPyMOL: PyMOL v1.8.2.2 software enhanced for Mac OS X (SchroÅNdinger LLC). Pilin truncations were introduced with PCR primers (Table 1) using as a template the pilA gene (GSU1496) of *G. sulfurreducens* cloned in the pTYB11 plasmid vector (IMPACT™-CN system, New England Biolabs). Table 1 shows primers (forward and reverse) used to clone the mature pilA sequence in the expression vector pTYB11 and PCR-amplified truncated derivatives (pilA$_n$). The resulting plasmids (pTYB11::pilAn, where n stand for the number of N-t amino acids truncated) were transformed into *E. coli* Rosetta™ 2 (DE3) pLysS cells (Novagen) for recombinant expression of the PilA$_n$ peptide fused at the N-t to an intein linker and a chitin-binding domain (CBD), as described elsewhere.

TABLE 1

| Plasmid | Primer sequence (5'-3')[1] | SEQ ID NO. |
|---|---|---|
| pTYB11::pilA | GGTGGTTGCTCTTCCAACT TCACCCTTATCGAGCTGCT | SEQ ID NO. 6 |
| | GGTGGTCTGCAGTCATTAA CTTTCGGGCGGATAGGT | SEQ ID NO. 7 |
| pTYB11::pilA10 | GGTGGTCTGCAGTCATTAA CTTTCGGGCGGATAGGT | SEQ ID NO. 8 |
| | GGTGGTTGCTCTTCCAACG CGATCATCGGTATTCTCGC | SEQ ID NO. 9 |
| pTYB11::pilA19 | GGTGGTTGCTCTTCCAACG CGATTCCGCAGTTCTCGGC | SEQ ID NO. 10 |
| | GGTGGTCTGCAGTCATTAA CTTTCGGGCGGATAGGT | SEQ ID NO. 11 |
| pTYB11::pilA20 | GGTGGTTGCTCTTCCAACA TTCCGCAGTTCTCGGCGTA | SEQ ID NO. 12 |
| | GGTGGTCTGCAGTCATTAA CTTTCGGGCGGATAGGT | SEQ ID NO. 13 |
| pTYB11::pilA22 | GGTGGTTGCTCTTCCAACC AGTTCTCGGCGTATCGTGT | SEQ ID NO. 14 |
| | GGTGGTCTGCAGTCATTAA CTTTCGGGCGGATAGGT | SEQ ID NO. 15 |

[1]Restriction sites (SapI, GCTCTTC; PstI, CTGCAG) are underlined.

Recombinant expression of CBD-PilA$_n$ fusion proteins in the *E. coli* host was in 1 L cultures of LB broth supplemented with 100 μg/ml ampicillin and 20 μg/ml chloramphenicol and incubated at 37° C. to an OD$_{600}$~0.4 before induction with 50 mM of isopropyl β-D-1-thiogalactopyranoside (IPTG) during overnight incubation at 16° C., as previously described. Cells harvested by centrifugation (4,000×g for 10 min) were resuspended in 20 mM Tris-HCl buffer (100 mM NaCl, 1 mM EDTA, 1% CHAPS) and lysed by tip sonication. Centrifugation of the lysate (12,000×g for 30 min at 4° C.) separated the soluble proteins with the fusion protein in the supernatant fraction. Purification of the fusion protein from the other soluble proteins was by affinity chromatography in a chitin column (New England Biolabs; ca. 40 ml bed volume) equilibrated with 200 ml of column buffer (20 mM Tris, 100 mM NaCl, 1 mM EDTA, pH 7.4). After incubation with the soluble protein fraction at room temperature for 20 min to promote the attachment of the fusion protein to the chitin matrix, we washed the column with 200 ml of buffer at increasing salt concentrations (20 mM Tris, 1 mM EDTA, 0.6/1 M NaCl pH 7.4) to remove the unbound proteins.

Cleavage of the $PilA_n$ peptides from the chitin-bound fusion protein was by induction of intein self-splicing with 50 mM 1,4-dithiothreitol (DTT). To do this, the column was incubated with ~200 ml of cleavage buffer (20 mM Tris, 100 mM NaCl, 50 mM DTT, pH 9) for 24, 48 or 72 h at room temperature (23° C.) or at 4° C. to minimize the aggregation of the peptide once cleaved from the solubility tag. A column wash with the same buffer but without DTT (elution buffer) eluted the $PilA_n$ peptides in 2-ml eluent fractions, which we identified by measuring the absorbance at 280 nm of the eluted fractions. Because some of the peptides aggregated after elution, cleavage efficiency was estimated from the ratio of the CBD over the full $CBD-PilA_n$ proteins retained in the chitin column after DTT cleavage and elution of the peptide. To do this, the chitin beads were removed from the column and resolubilized the chitin-bound proteins in 1% SDS at 100° C. Separation of the solubilized proteins was in a 7.5% Tris/glycine SDS-PAGE (Bio-rad) run for 30 min at 200 V in Tris/glycine/SDS buffer (25 mM Tris, 192 mM glycine, 0.1% w/v SDS) using a Bio-rad Mini Trans-Blot cell system. The proteins in the gels were stained with Bio-safe Coomassie (Bio-rad, Hercules, CA) for 1 h and destained in $ddH_2O$. The density of the fast migrating band (CBD module) and the slower migrating $CBD-PilA_n$ protein band was used to calculate the percent of $CBD-PilA_n$ that was cleaved.

Cleavage at room temperature for 24 h was optimal for high-yield cleavage of $PilA_{19}$ and used thereafter. Peptide-containing fractions were pooled before estimating the protein concentration by absorbance at 280 nm using a Nano-Drop™ spectrophotometer (Thermo Scientific). SDS-PAGE was used to monitor the recombinant expression of the fusion protein ($CBD-PilA_n$) and purity of the $PilA_n$ peptide eluting from the chitin column using 10-20% Tris-Tricine polyacrylamide gels run for 75-120 min at 100V in Tris/tricine/SDS buffer (100 mM Tris, 100 mM Tricine, 0.1% w/v SDS). Proteins in the tricine gels were fixed for 30 min with an aqueous solution of 50% methanol and 40% acetic acid prior to staining with Bio-safe Coomassie (Bio-rad, Hercules, CA) for 1 h and de-staining with $ddH_2O$ until bands were visible. The mass of the peptide was confirmed by Matrix Assisted Laser Desorption-Ionization-Time of Flight (MALDI-TOF) mass spectrometry using a 1 µl peptide solution mixed with 1 µl of 50 mM 3,5-dimethoxy-4-hydroxycinnamic acid in 50% acetonitrile $CH_3CN/0.5\%$ trifluroacetic acid (TFA) and dried on a sample plate. Mass spectra collection was on a time-of-flight (TOF) Voyager-DE Pro-MALDI-TOF mass spectrometer (Applied Biosystems, Framingham, MA).

Circular Dichroism (CD). $PilA_{19}$ peptides purified in elution buffer were dialyzed against 10 mM potassium acetate buffer (with 50 mM $Na_2SO_4$, pH 3.8) using Spectra/Por® Biotech cellulose ester dialysis membranes (MWCO 100-500 Da). The peptide concentration was determined from the difference spectrum (320 to 270 nm) of the protein dissolved in 1 ml of 6 M guanidine hydrochloride at pH 12.5 versus pH 7.1 (39) and with the known molar extinction coefficients of tyrosine and tryptophan residues (40) using the equation:

$$c = \frac{A_{293}}{2,357Y + 830W} \quad \text{(eq. 1)}$$

where $A_{293}$ is the absorbance at 293 nm in the difference spectrum, Y is the number of tyrosine (3 in $PilA_{19}$) and W is the number of tryptophan (0 in $PilA_{19}$) residues.

The concentration of the peptide in the buffer was adjusted to approximately 50 µg/ml prior to CD spectroscopy. When indicated, sodium dodecyl sulfate (SDS) was added to the peptide solution at a final concentration of 1, 8 or 40 mM. The peptide solutions were dispensed in a quartz cuvette (0.1 cm path length, Starna Cells Inc.) and their CD spectrum in the 190 to 360 nm was collected at 0.5 nm increments (5 second integration time) using a Chirascan™ spectrometer (Applied Photophysics Ltd., Leatherhead, United Kingdom). The spectra were baseline-corrected and smoothed using a third order Savitsky-Golay filter. The CD instrument units (θ, millidegrees) were converted into mean residue molar ellipticity [θ] units using the Wallace and Janes equation (41):

$$[\theta] = \left(\frac{\theta \times 0.1 \times MRW}{c \times l}\right) \quad \text{(eq. 2)}$$

where c is the peptide concentration in mg/ml, l is the path length of the cuvette in cm (0.1 cm), and MRW is the mean residue weight of the sample estimated from the molecular mass MW in Daltons (4,524 Da for $PilA_{19}$) and the number n of amino acid residues (42 for $PilA_{19}$), as follows:

$$MRW = \frac{MW}{n-1} \quad \text{(eq. 3)}$$

The CD data was used to estimate the α-helix content of peptide using the program CONTINLL at the DICROWEB server. The program is a modification of the CONTIN method that uses a ridge regression algorithm to estimate the CD spectrum of unknown proteins by comparison to a linear combination of CD spectra of N reference proteins with known conformations. Because the reference proteins are predominantly globular, the conformation estimates for peptides, fibrous proteins, and membrane proteins are approximate. The program evaluates the goodness of fit parameter normalized mean residue standard deviation (NMRSD), which is defined as:

$$NRMSD = \left[\frac{\sum(\theta_{exp} - \theta_{cal})^2}{\sum(\theta_{exp})^2}\right]^{1/2} \quad (3.4)$$

where $\theta_{exp}$ and $\theta_{cal}$ are the experimental and calculated ellipticity values at a specific wavelength. A NRMSD value of less than 0.1 is generally considered a good fit. Thus, NRMSD values above 0.1 were rejected.

The CD spectra were also collected for fibers assembled with recombinant $PilA_{19}$ peptides resuspended for 30 min in 10 mM potassium acetate with 50 mM $Na_2SO_4$ (pH 7). A 500 µl aliquot of a 40 µg/ml (Nanodrop estimate) of the pili solution was dispensed into a quartz cuvette with a 1 mm path length (Starna Cells Inc., Atascadero, CA) and scanned from 190 to 260 nm at 0.5 nm increments with a 5 second integration time with automated baseline subtraction. Native pili purified from *G. sulfurreducens* were used as controls before or after denaturation with 8 M urea. All the scans were adjusted from θ, millidegrees, to molar ellipticity using equation, as described above.

In vitro assembly of $PilA_{19}$ pilins. $PilA_{19}$ fibers were synthesized in a protocol that incorporated a buffer exchange step to resuspend the peptides in assembly buffer (80:20, acetonitrile:methanol) and evaporation-induced assembly in the presence of a hydrophobe. The standard protocol for maximum yields of fiber formation with $PilA_{19}$ used a reverse phase C18 column (Sep-Pak C18 3 cc Vac Cartridge, 55-105 μm Particle Size, Waters Corporation, Milford, MA) for buffer exchange inside an anaerobic chamber (COY Labs). The resin in the cartridges was first hydrated with 5 ml of acetonitrile and equilibrated with 5 ml of $ddH_2O$, following manufacturer's recommendations. A solution of the recombinant peptide (8 mg of $PilA_{19}$ in ~10 ml of elution buffer) was applied to the column by gravity flow and the peptide retained in the C18 resin was washed with 5 ml of $ddH_2O$ (1.7× column volume) before elution in a disposable glass tube with 3 ml of a freshly prepared assembly buffer. When indicated, the washing step was extended from 5 to 9, 12, 15 or 18 or 15 ml of $ddH_2O$. DTT and C18-silica particles co-eluting with the peptide were identified in the UV-vis spectrum of the solution as absorbance peaks at 205 nm (DTT) and 245 nm (silica) using a Shimadzu UV-2401PC spectrophotometer. Control solutions with pure silica particles demonstrated the sensitivity of the detection method to particle sizes of less than 1 μm (FIGS. 6C-6D). Standard of pure silica particles 0.5-1 μm in diameter were used to calculate the concentration of C18-silica particles in the solution.

When indicated the buffer exchange step was carried out in an Oasis Max™ extraction cartridge (60 mg of non-silanol polymeric sorbent functionalized with a quaternary amine sorbent, Waters Corporation, Milford, MA). The column was hydrated with 1 ml of acetonitrile and washed with 1 ml of $ddH_2O$ before loading the 2 ml of the peptide solution previously adjusted to a pH of 10 with 1 mM NaOH. After washing the column with 1 ml of 5% $NH_4OH$, the peptide was eluted with 1 ml assembly buffer and the UV-vis spectrum was collected to analyze the column eluant, as described for the C18-column eluants. Peptides eluted from these columns required the addition of a hydrophobe (octadecane, 1:100 aqueous solution) to promote fiber formation.

The standard protocol for evaporation-induced self-assembly started with a 1-ml aliquot of the peptide solution (~8 mg) containing the hydrophobe (e.g., 1:100 octadecane or C18-silica particles) in assembly buffer and a first round of evaporation for 30 min at 45° C. in a Savant™ Speed-Vac™ concentrator (SPD121P model, Thermo Fisher). Fiber elongation was controlled through refeeding steps every 30 minutes (4 times with 500 μl of the peptide solution) and reaction mixing by aspiration with a micropipette. At the end of the evaporation process, the dried sample was resuspended in 200 μl of $ddH_2O$ and dispensed in 50 μl aliquots. Addition of 200 μl ice cold acetone to each aliquot and overnight incubation at −20° C. precipitated the fibers, allowing to recover them by centrifugation (1 h, 4° C. in a microcentrifuge). After a final drying step under a stream of $N_2$, the sample was stored at −20° C. until further use. When indicated, the final drying step was via lyophilization in order to measure the average particle size of the sample via dynamic light scattering (DLS) in a Malvern Zetasizer Nano-ZS (0.3 nm to 10 microns sensitivity). Assembly efficiency was also calculated as the difference of free $PilA_{19}$ monomer in solution before and after assembly, based on protein concentrations measured by absorbance at 280 nm in a NanoDrop™ spectrophotometer (Thermo Scientific) using a standard curve of bovine serum albumin (BSA).

Scanning Probe Microscopy. Conductivity studies were conducted in a clean room using $PilA_{19}$ fibers stored dried at −20° C. and rehydrated in 200 μl of $ddH_2O$ at 4° C. for 12-18 h. Deposition for 10 minutes of 10 ill aliquots of the solution onto the surface of a freshly-cleaved Highly Oriented Pyrolytic Graphite (HOPG; SPI Supplies) promoted the adsorption of the fibers to the electrode. Absorbent lens paper wicked off excess fluid while two washes with 10 μl of $ddH_2O$ removed impurities from the HOPG surface. Samples were allowed to dry in a sealed container at room temperature for approximately 10 minutes before imaging the samples in tapping mode by Atomic Force Microscopy (AFM) with an Asylum Research Cypher S system equipped with an AC240TS tip (Asylum Research). Electrode surface scans were typically of 10×10 μm² to locate the area of sample deposition and image several fields randomly that best represented the distribution of fibers on the surface. The AFM images were analysed with the free hand tool of ImageJ to measure the length of the fibers. Conductive probe AFM (CP-AFM) analyses, which measures the transversal conductivity of the sample from the electrons flowing between the conductive AFM tip and the HOPG electrode, followed protocols previously used to measure the conductivity of the native pili. As controls, we also conducted AFM topographic and CP-AFM conductivity analyses of the native PilA pili, which were purified as reported elsewhere. The ±100 mV ohmic region in the IV plots was fitted to a linear regression line using the Igor Pro 6 software to calculate the electrical resistance of the fibers at biological voltages. Analyses of the asymmetry of the IV plots was via rectification scores (ratio of current recorded at the positive over the negative voltage) calculated at voltages comparable or exceeding the biological-relevant voltage (100 and 600 mV, respectively) as reported elsewhere. A rectification score below 1 indicates asymmetric current flow that favors the electrode-to-tip direction, thus electrons flowing from the fiber towards the external electron acceptor.

Scanning Tunnelling Microscopy (STM) analyses (imaging and spectroscopy) used the same AFM instrument but equipped with a mechanically cut Pt:Ir STM tip (Asylum Research) and operated in STM mode. The quality of the STM tip was tested in scans on the freshly cleaved HOPG surface prior to depositing and scanning the pili samples (sample voltage of 500 mV; current set point of 350 pA). Sample deposition was with hydrated or glutaraldehyde-fixed $PilA_{19}$ fibers, using protocols described for the deposition of hydrated or chemically-fixed native PilA pili. IV plots collected the current tunnelling through individual fibers at a set point of 10 pA, with the tip held at ground, while sweeping the bias voltage (±0.6 V) of the HOPG substrate. The linearity of the plot in the ±100 mV ohmic region was analyzed by the fit of a linear regression line with the Igor Pro 6 software. The asymmetry of the STM IV plots and the material's electron band gap were assessed in plots of the derivative of the current and voltage data points (dI/dV) versus the sample voltage (V).

Example 1—Design, Recombinant Production and Structural Characterization of Pilin Building Blocks Computational analyses of the PilA sequence via AGGR-ESCAN (14) identified two regions in the peptide (residues 1-22 and 25-31) with highest aggregation propensity (FIG.

1B). Aggregation scores were particularly high for the first 10 amino acids, which are also among the most hydrophobic residues identified in a Kyte Doolittle plot (15) (FIG. 1B). The aggregation and hydrophobicity analyses predict truncations of the first 21-22 amino acids as having the highest impact on solubility. As this extended truncation preserves the aromatic and charged residues required for fiber formation and conductivity (FIG. 1B), this N-t region was targeted to engineer pilin derivatives suitable for recombinant expression with a self-splicing intein linker and a solubility and affinity tag (Chitin Binding Domain or CBD). The recombinant approach reproducibly recovered in the soluble fraction of culture lysates fusion proteins containing pilins engineered with truncations of 10, 19, 20 and 22 amino acids (FIG. 1B-D).

Affinity chromatography in a chitin column retained the fusion proteins bound to the chitin matrix and permitted the elution of the pilin peptide after inducing the self-splicing of the intein linker with dithiothreitol (DTT) (FIG. 4A). FIG. 4A shows, as an example, the enrichment of the CBD-PilA$_{19}$ fusion protein in soluble fractions collected from replicate culture lysates and the purification of the PilA$_{19}$ peptide after incubating the chitin-bound CBD-PilA$_{19}$ protein with DTT at room temperature (23° C.) for 24 h.

While the amount of recombinant fusion proteins recovered from the soluble culture fractions was similar for all the truncated pilins, the amount of peptide eluted from the affinity column after DTT cleavage varied widely (FIG. 2). Cleavage efficiency via intein self-splicing is sensitive to temperature and to the peptide residues adjacent to the intein linker. Increasing the temperature from 4° C. to 23° C., for example, improved the cleavage efficiency for all the PilA$_n$ peptides but also promoted the aggregation of the most hydrophobic peptide (PilA$_{10}$) once cleaved. As a result, the amount of PilA$_{10}$ recovered in solution was too low for visualization by SDS-PAGE and required detection via MALDI-TOF mass spectrometry (FIG. 3).

By contrast, truncating 19 amino acids (PilA$_{19}$) permitted the high-yield recovery of the PilA$_{19}$ peptide after cleavage from the CBD tag (FIG. 4A). The 19-amino acid truncation fused the peptide to the intein linker via a residue (alanine) (FIG. 1B) that is optimal for intein self-splicing. As a result, cleavage efficiency was higher for PilA$_{19}$ than for any other soluble peptides (PilA$_{20}$ and PilA$_{22}$), allowing for the nearly complete recovery of the peptide in the column eluant (FIG. 2). In addition to enabling the highest biosynthetic yields, PilA$_{19}$ retained the helical conformation that is critical for self-assembly and fiber formation once in the presence of a hydrophobe. The folding dynamics of the PilA$_{19}$ was investigated by circular dichroism (CD) as a function of the concentration of a detergent such as SDS in the peptide solution (FIG. 4B). The far UV CD spectrum of the peptide in 10 mM potassium acetate buffer at pH 7 showed very low ellipticity above 210 nm and a strong negative signal around 200 nm, consistent with a disordered peptide. But addition of SDS shifted the CD spectrum and revealed the characteristic maxima (at ~190 nm) and minima (at ~208 and ~222 nm) of α-helical conformations. Furthermore, the intensity of the positive (190 nm) and negative (208 nm and 222 nm) helical signals reached maxima at or above the critical micellar concentration (CMC) of the detergent (~8 mM in water) (19, 20) (FIG. 4C). At this threshold concentration, SDS recreates the hydrophobic environment of the inner membrane, where the pilins are stored prior to assembly to stabilize their α-helical conformation.

Concentrations at or above the CMC (8 mM and 40 mM) also produced intensity ratios of 222 nm over 208 nm (~0.7) close to the 0.8 ratio expected for a single-stranded α-helix (22). As the peptide has a negative net charge of −1.1 at neutral pH, we minimized electrostatic effects by collecting CD spectra of control solutions at a pH of 3.8. At this acidic pH, below the theoretical isoelectric point (pI, 4.86) of PilA$_{19}$, the peptide has a net positive charge of +3.2 that cancels out electrostatic repulsion forces with the anionic detergent. The intensity of the α-helical signature peaks was greater at pH 3.8 than at pH 7 (FIG. 4C). The more favorable electrostatic interactions between the peptide and the detergent at the acidic pH also increased the pilin's helical content (from ~45% to 56% at or above the CMC and from 27% to ~49% below the CMC). The increased helical content of the PilA$_{19}$ peptide at the acidic pH also increased the intensity ratio of the 222 nm and 208 nm peaks to ~1, consistent with the assembly of 2 or more α-helices in coiled coil configurations. These results demonstrated that PilA$_{19}$ can adopt the helical conformation that is critical for pilin self-assembly and electronic coupling in the pilus fiber. Additionally, the studies highlighted the critical role that hydrophobicity and electrostatics have in modulating the folding and self-assembly of the peptides.

Example 2—Fiber Formation Via Self-Assembly of PilA$_{19}$ Peptides

Figures 9A, 9B:
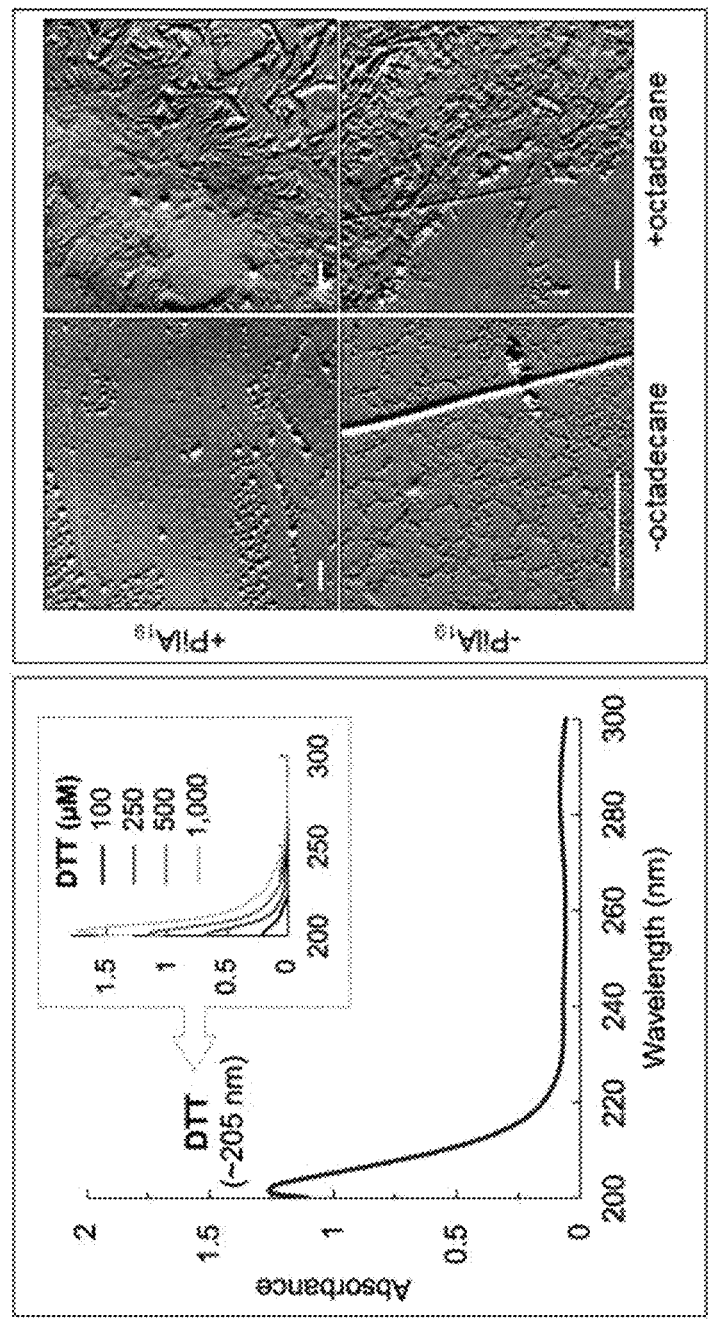
FIG. 9A is a plot of induction of PilA$_{19}$ fiber formation with octadecane. The plot is UV-vis spectrum of eluent collected from an Oasis Max™ exchange cartridge after a buffer exchange showing the presence of DTT (205 nm, inset shows standard curve).
FIG. 9B is an image of a tapping mode AFM showing PilA$_{19}$ fiber formation in the presence of octadecane (1:100 aqueous solution) when using Oasis Max™ cartridges for peptide buffer exchange. Controls without PilA$_{19}$ show the resin residues and an octadecane layer on the electrode surface. Scale bar, 1 µm.

The helical folding of PilA$_{19}$ and subunit assembly in solution was investigated. Hydrophobic conditions optimal for controlled self-assembly of the PilA$_{19}$ peptides into fibers was studied. FIG. 5A shows the main steps of the protocol optimized for bottom-up fabrication of PilA$_{19}$ fibers. The fabrication protocol starts with a buffer exchange step that resuspends the peptides in a buffer of acetonitrile and methanol suitable for evaporation-induced self-assembly in the presence of a hydrophobe. Acetonitrile has lower polarity than water to help maintain recombinant pilin peptides in solution. Methanol is known to stabilize helical peptide conformations in solution. Addition of a hydrophobe triggered self-assembly of the peptides, whereas controlled evaporation of the solvent increased molecular crowding and facilitated peptide-peptide interactions needed for fiber formation (FIG. 5A). Octadecane, a straight-chain alkane hydrocarbon of 18 carbon atoms (C18), was a suitable hydrophobe to promote the nucleation of the pilins and fiber formation (FIG. 9A-9B). Atomic Force Microscopy (AFM) imaging of the octadecane-triggered assembly reaction revealed, however, an extensive coating of the fibers and underlying electrode by a hydrocarbon layer that prevented conductivity measurements (FIG. 9A-9B). To bypass this limitation, the octadecane was replaced with silica particles functionalized with a coating of the nucleating octadecyl carbon chains (C18) (FIG. 5A-5C). By carrying out the buffer exchange step in a reverse phase column packed with a reverse phase resin of C18-silica particles (55-105 μm in diameter), the PilA$_{19}$ peptide was simultaneously eluted and nucleating C18-silica particles approximately 25-50 nm for hydrophobe-triggered fiber formation (FIG. 6A-6D).

The hydrophobe may also be added after a buffer exchange step in a different matrix. A buffer exchange step was conducted in an Oasis Max™ exchange cartridge containing 60 mg of non-silanol polymeric sorbent functionalized with a quaternary amine sorbent (Waters Corporation, Milford, MA). The column was hydrated with 1 ml of acetonitrile and washed with 1 ml of ddH$_2$O before loading the 2 ml of the peptide solution previously adjusted to a pH of 10 with 1 mM NaOH. The column-bound peptide was washed with 1 ml solution of 5% NH$_4$OH and eluted with 1 ml solution of assembly buffer. FIG. 9 shows the UV-vis spectrum of eluent collected from an Oasis Max™ exchange cartridge and the induction of pilin assembly in the evaporation step with the addition of octadecane. The UVvis spectrum shows the DTT peak carried over with the pilins (from the affinity purification step in a chitin column), but no silica (~245 nm). Addition of octadecane (1:100 aqueous solution) to the peptide solution formed assembly composition followed by the standard evaporation/refeeding/mixing protocol (FIG. 5A) was required to trigger fiber formation (FIGS. 9A-9B).

Insights into the rate-limiting steps of $PilA_{19}$ assembly was gained by investigating the effect of hydrophobe concentration in fiber formation. For these experiments, Dynamic Light Scattering (DLS) was used to grossly estimate fiber size in reactions with different concentrations of the C18-silica particles and AFM to image the structural features of the assemblies (FIG. 5B). C18-silica particle concentrations of ~3.5 mM triggered fiber formation (FIG. 5B) and permitted maximum assembly efficiencies (40-55% of the pilin monomers assembled as fibers). Efficient assembly also required reaction mixing. Thus, unmixed assembly reactions with optimal concentrations of the nucleating C18-silica particles produced fibers 1(±0.5)-μm long and assembly efficiencies as low as 14% (FIG. 5C). However, mixing the assembly reactions by aspiration with a micropipette during the peptide refeeding steps promoted the assembly of the pilins and increased fiber length to 6(±1)-μm long (FIG. 5C). This suggests that the initial evaporation step of a 1 ml volume of assembly buffer with the peptide (~3 mg) stimulated pilin nucleation by the C18-silica hydrophobe, and four sequential peptide refeeding steps (total of 6 mg of peptide) with mixing increased the number of nucleation sites available for peptide assembly and the availability of peptide building blocks to grow the fibers. Controls with mixing but suboptimal concentrations of the hydrophobe (0.2 mM) resulted in the formation of small aggregates interspersed with short fibers (FIG. 5B). Thus, fiber elongation is both dependent on hydrophobe concentration and reaction mixing. Additional refeeding/mixing did not change the kinetics of fiber formation, suggesting that an equilibrium between free peptide and fibers had been reached that prevented new nucleation and elongation reactions.

Figures 7A, 7B, 7C, 7D, 7E, 7F:
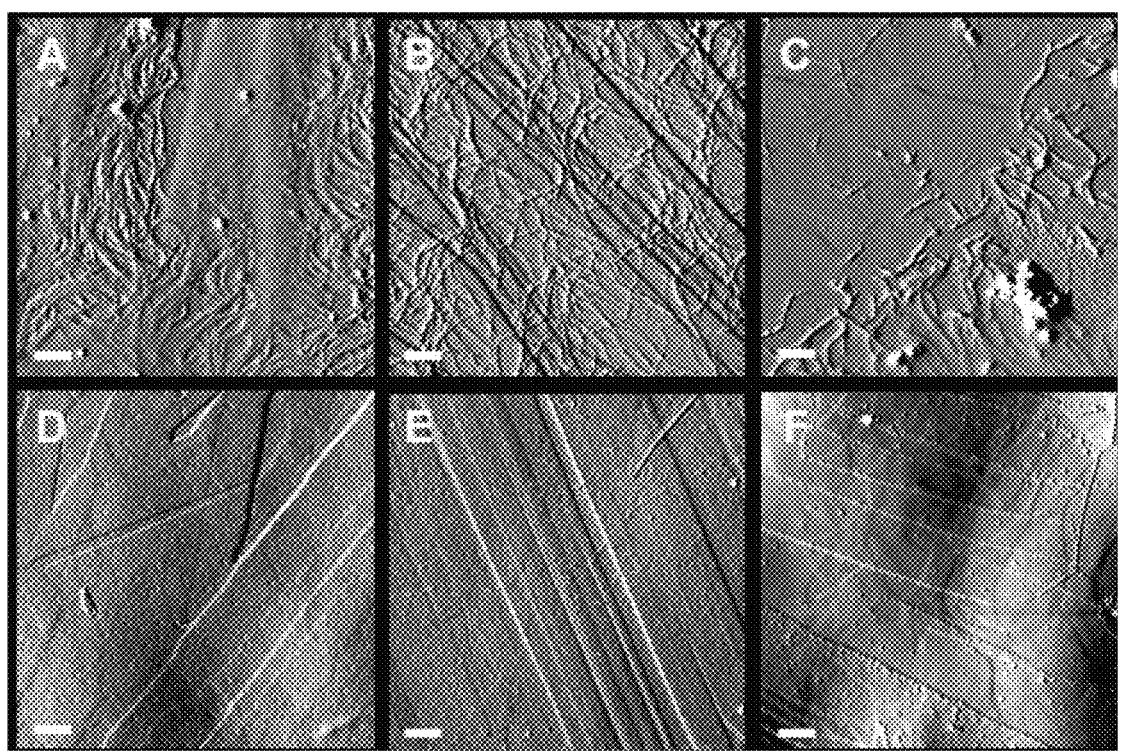
FIGS. 7A-7F are images showing the effect of C18-column pre-wash.

By adjusting the washing steps to the column prior to peptide elution, the concentration of the hydrophobe in the assembly buffer was modulated prior to assembly and the requirement of the hydrophobe to promote fiber formation (FIGS. 7A-7F). Extending the washing step from 5 ml to 15 ml retained sufficient hydrophobe to stimulate fiber formation under these conditions but washes with 30 ml of $ddH_2O$ reduced the C18-silica particles that co-eluted with the peptide and yields of fiber formation. FIGS. 7A-7F show the effect of C18-column pre-wash. FIG. 7A, FIG. 7B and FIG. 7C show the effect on $PilA_{19}$ fiber formation with 5 ml, 15 ml or 30 ml, respectively, of $ddH_2O$. Separate C18-columns were washed with 5 ml (standard protocol), 15 ml, and 30 ml of $ddH_2O$ to reduce the amount of loosely-bound C15-silica particles coeluting with PilA 19 during the buffer column exchange step. After buffer exchange with a $PilA_{19}$ solution (FIGS. 7A-7C) or a buffer-only control (FIGS. 7D-7F), the eluents were subjected to the evaporation induced assembly protocol and samples deposited on highly oriented pyrolytic graphite (HOPG) were imaged with an AFM operated in tapping mode.

Example 3—Biochemical and Electronic Characterization of $PilA_{19}$ Fibers

Figure 8C:
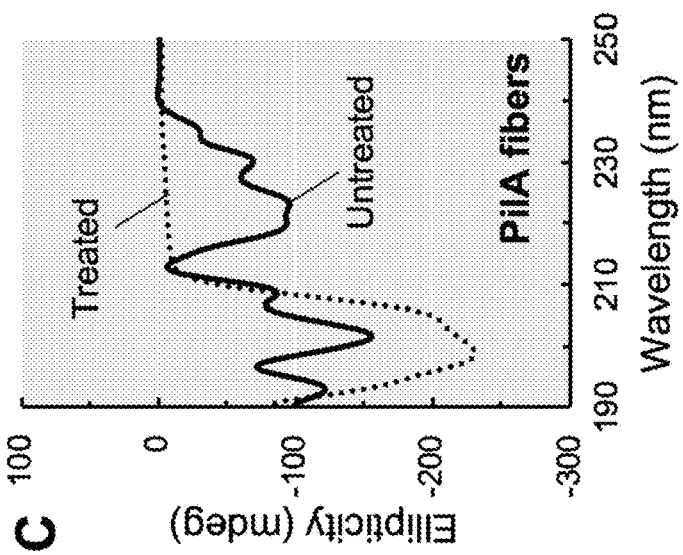
FIG. 8C is a plot of CD spectra of native pili treated with Urea (8M urea; dash) or untreated (solid line).
Figure 8B:
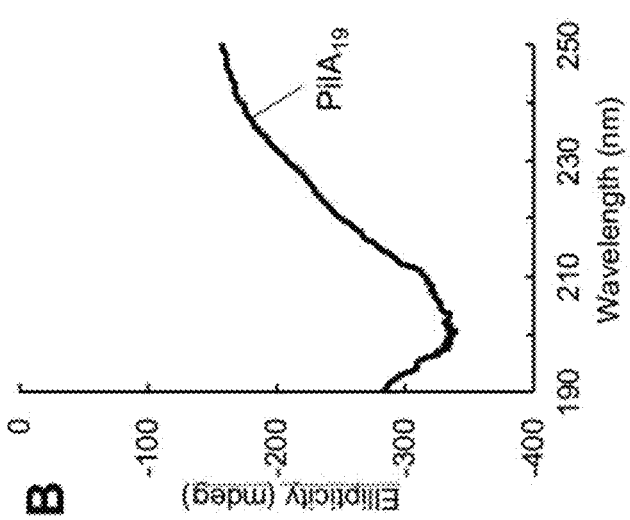
FIG. 8B is plot of CD spectra of recombinant pili.
Figure 8A:
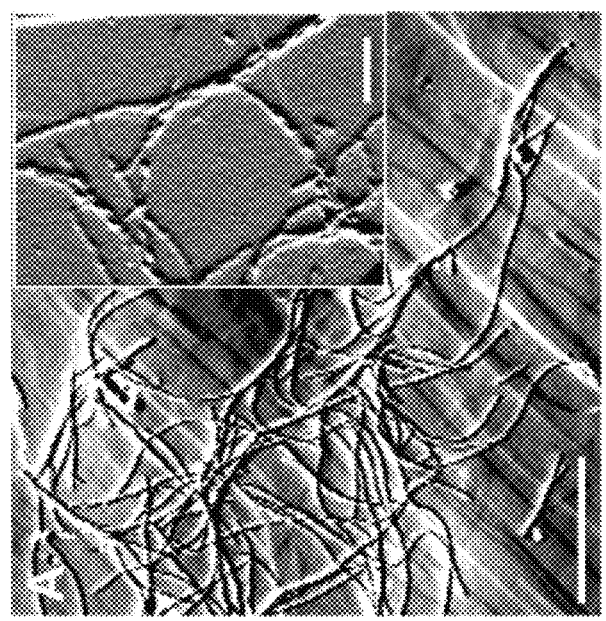
FIG. 8A is an image of AFM imaging of $PilA_{19}$ fibers assembled in vitro. Inset shows single fibers and braided supramolecular structures with line scans used to determine the AFM height (top, dark gray bar points to a single fiber; bottom lighter gray bar points to braided fibers). Scale, 0.2 µm.

The optimized hydrophobe-triggered assembly protocol, with sequential refeeding and mixing steps, consistently produced long, flexible fibers. The average diameter of the $PilA_{19}$ fibers (calculated as AFM height) was ~2 nm, which is the same as that reported for the native PilA pilus fibers. AFM images of the $PilA_{19}$ fibers also revealed some supramolecular structures (braids of two fibers), but most of the fibers were present as well dispersed filaments in aqueous media (FIG. 8A). This contrasts with the extensive supramolecular aggregation of native pili even after minimizing the pili's surface electrostatics in alkaline buffers. The good dispersion of the $PilA_{19}$ fibers also permitted the collection of CD spectra (FIG. 8B) similar to the CD profiles of other bacteria Type IVa pili. From the CD spectrum of the $PilA_{19}$ fibers, an intensity ratio of 222 nm over 208 nm absorbance of 0.75 was calculated, which is close to the ~0.8 intensity ratios that result from the α-helical conformation of the peptide monomers. By contrast, the CD spectra of control solutions with the native pili were convoluted by numerous peaks (FIG. 8C) and had intensity ratios at 222 and 208 nm of ~1, as reported for supramolecular assemblies. This complex spectral profile results from the random aggregation of the native pilus fibers, which form thick bundles that can only be destabilized with strong denaturants such as urea (FIG. 8C). The aggregative nature of the native pili is the result of surface electrostatics as well as fiber length, which can be greater and more heterogenous than in samples of ~6-μm long $PilA_{19}$ fibers.

Figures 10A, 10B, 10C, 10D, 10E, 10F, 10G, 10H:
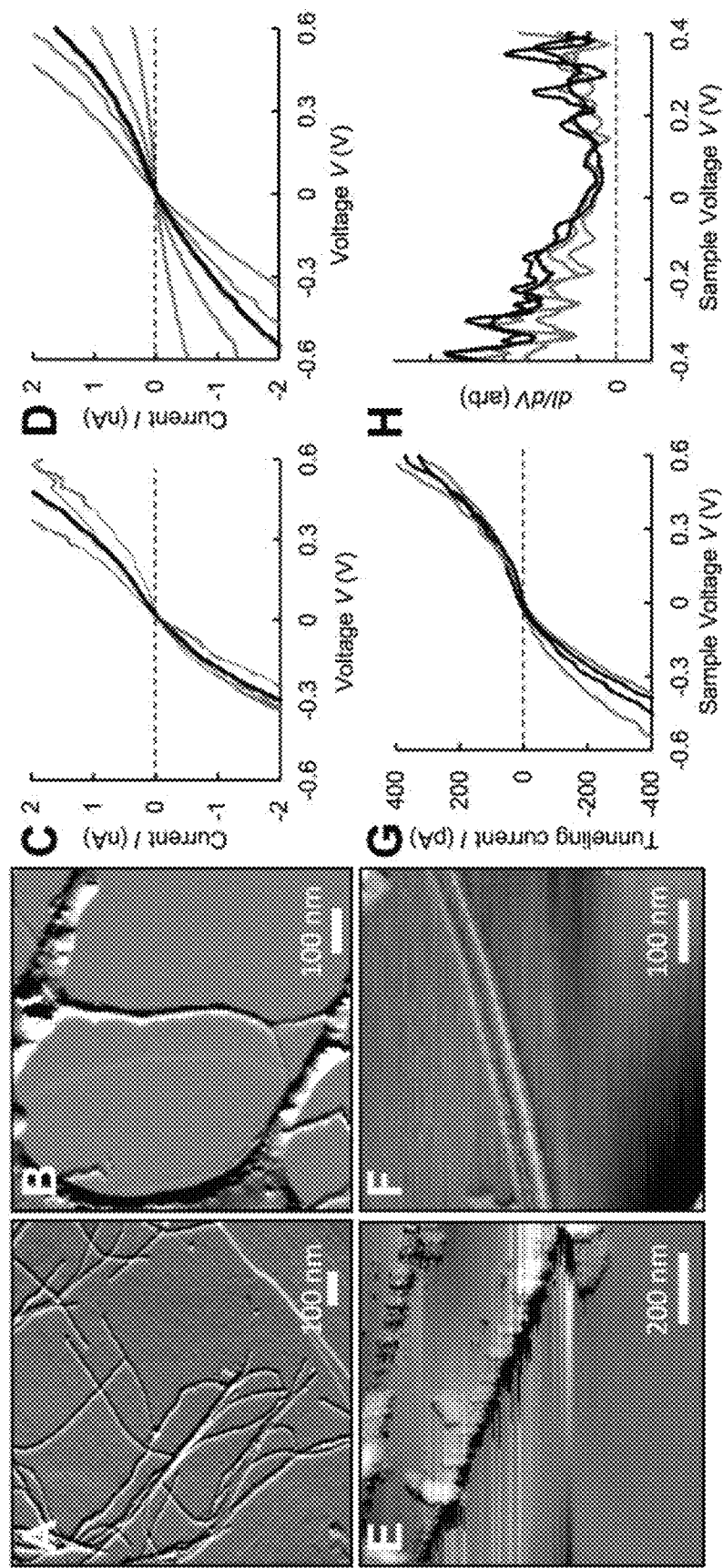
FIGS. 10A-10H are images and plots of electronic characterization of recombinant pili.

The dispersion of the $PilA_{19}$ fibers in aqueous media also facilitated AFM imaging of individual filaments after deposition onto freshly cleaved highly oriented pyrolytic graphite (HOPG) (FIG. 10A). Control samples with the native *G. sulfurreducens* pili (denoted PilA fibers), on the other hand, showed extensive supramolecular aggregation that made the identification of single filaments more laborious (FIG. 10B). Further, the reduced aggregative nature of the $PilA_{19}$ fibers improved electrical contact with the underlying electrode. As a result, conductive probe AFM (CP-AFM) measurements of the transversal current flowing through different fibers while sweeping the applied voltage (I-V) were less variable than with PilA fibers (FIG. 10C). Average IV curves from four independent $PilA_{19}$ fibers were, however, similar to those representative of PilA fibers (FIG. 10C-10D). Furthermore, the average resistance of the $PilA_{19}$ fibers (~900 MOhms at ±100 mV), was within the orders calculated for the native wires (~925 MOhms). I-V curves collected for the $PilA_{19}$ and PilA fibers by CP-AFM were also similarly asymmetric, showing a rectification behavior such that more current was measured at negative voltages than at the same positive voltages (FIG. 10C-10D). Thus, the average rectification score (calculated as current at positive over negative voltage) for the $PilA_{19}$ fibers was ~0.5 and 0.7 at biological (±100 mV) and higher (±600 mV) voltages. Similarly, the PilA fibers had rectification scores below 1 (~0.7) at both. Thus, current flow through the pilus is more efficient in the electrode to the tip (more current produced at negative voltages), which is also the biological path for the discharge of respiratory electrons from charged electron carriers in the cell envelope to the pilus and then to extracellular electron acceptor.

Scanning tunneling microscopy (STM) was used to characterize nanoscale spatial variations in electronic properties within individual $PilA_{19}$ fibers (FIG. 10E). The higher spatial resolution of the STM technique compared to CP-AFM resolved beadlike structural features in the $PilA_{19}$ fibers previously described for the native PilA pili. The bright spots are regions of the fiber with higher local electronic density of states and, thus, regions that supply more tunneling current. The molecular substructures identified in the PilA$_{19}$ fibers have periodicities that match well with those reported for the grooves and ridges that form the surface landscape of the native pili. The STM diameter estimated for the PilA$_{19}$ fibers (~5-7 nm) was also within the ranges reported for the native PilA filaments prior to deconvoluting for the broadening tunneling effect caused by the tip when scanning a nanowire. Also as reported previously for the PilA filaments (28), STM imaging of the PilA$_{19}$ fibers improved with a chemical fixation step (FIG. 10F). The chemical treatment immobilized more fibers onto the surface and improved electrical contact with the electrode. As a result, the interactions between the STM tip and the biomaterial were more stable when probing chemically-fixed PilA$_{19}$ fibers, producing cleaner STM topographic images (FIG. 10F).

Yet chemical fixation did not substantially affect the measured conductivity, as indicated by the overlapping I-V curves collected when probing fixed locations of untreated (hydrated) and chemically-treated PilA$_{19}$ fibers while sweeping the voltage at ±600 mV (FIG. 10G). Additionally, the STM I-V curves of untreated and treated fibers reproduced the ohmic response of the biomaterial in the ±100 mV biological voltage range observed by CP-AFM and had similar slopes, thus a similar resistance to the passage of electrons. Plots of the differential conductance (dI/dV) of the untreated and treated PilA$_{19}$ fibers versus the tip-sample bias voltage (V) confirmed these similarities and revealed electronic states at low voltages that never reach zero conductance (FIG. 10H), a distinctive electronic feature of the native PilA pili that results from a very small electron band gap. The STM differential conductance plots also confirmed the asymmetric conductance reported for native pili, as expected for a biomaterial that favors current flow from negative to positive voltages, even at the low voltages (i.e., ±100 mV) that drive the flow of respiratory electrons through the pili and onto the iron oxides (29).

Discussion

The recombinant production of peptides derived from the conductive pilin of *G. sulfurreducens* permitted the synthesis at high yields of a soluble pilin peptide (PilA$_{19}$) carrying an N-t truncation of the first 19 amino acids of the mature PilA pilin. The truncated peptide lacks hydrophobic amino acids at the N-t that are known to participate in biological assembly processes (e.g., F1 and E5) (FIG. 1), but it retains the α-helical conformation that is needed for pilin-pilin hydrophobic interactions and self-assembly. Importantly, the PilA$_{19}$ truncation preserved the charged residues of the pilin that MD simulations predict to form salt bridges between neighboring pilins (FIG. 1), establishing intermolecular bonds critical to the structural integrity of the fiber core and the electronic coupling of aromatic side chains. Supporting the computational predictions, the recombinant PilA$_{19}$ peptide self-assembled into a conductive fiber that exhibits biochemical, structural and electronic properties similar to a native PilA pilus.

Octadecane, whether in solution (FIG. 9A-9B) or immobilized on silica particles (FIG. 5A), was a suitable hydrophobe to trigger pilin nucleation and fiber formation. The addition of the hydrophobe in a surface-constrained form also permitted its separation from the fibers by centrifugation at the end of the assembly reaction. The emission of silica from nanosized particles in a precise region of the UV spectrum (FIG. 6A) also proved useful to optimize the concentration of hydrophobe. PilA$_{19}$ fibers were synthesized of approximately 6-μm long that dispersed well in mild aqueous solutions (FIG. 5A-5C). This contrasts with purification protocols available for native pili, whose longer and heterogeneous length promotes the formation of large supramolecular structures that are difficult to disrupt without denaturing the pilus fiber core (FIG. 5A). The reduced aggregation of the PilA$_{19}$ fibers also facilitated their deposition on electrode surfaces and electronic characterization by scanning probe methods (FIG. 10A-10H). Reproducible electronic probing of hydrated fibers by CP-AFM is challenging, inasmuch as hydration affects the electrical contact with the underlying electrode surface and the measured conductivity. Supramolecular aggregation in the native PilA pili enhances these effects and the variability of the conductivity measurements compared to the more dispersed PilA$_{19}$ fibers (FIG. 10A-10H). Despite these differences, scanning probe methods calculated a similar average electrical resistance for the PilA and PilA$_{19}$ fibers (900-925 MOhms) and revealed the characteristic topographic periodicities (roughly every 10 nm) that arise from the conserved helical arraignment of the pilins. The contact resistance was reduced between the fibers and the underlying electrode and, therefore, sample-to-sample variability through chemical fixation FIG. 10A-10H Importantly, the chemical treatment did not affect the conductive properties of the fibers, a property that can facilitate the integration of the protein nanowires with inorganic nanomaterials in electronic devices.

Also important for applications in bioelectronics is the rectifying properties of the PilA$_{19}$ fibers, which like the native PilA pili transport charges more efficiently from negative to positive voltages FIG. 10A-10H). Rectification could reflect mechanistic differences in the directionality of charge transport through the pilus that favor the biological flow of electrons from the cell envelope to the pilus-bound electron acceptor.

The demonstration that truncated, conductive Type IV pilins can be expressed in heterologous hosts, purified, and then self-assembled in vitro to form fibers having an electrical conductivity comparable to the native pili confirms unequivocally that a peptide assembly can conduct electrons in the absence of metals and/or organic redox cofactors. The production of conductive nanowires also represents a significant milestone in the field of bioelectronics in that it establishes a versatile new platform for bottom-up fabrication of nanowires that leverages powerful, synergistic tools to customize the properties of the biomaterial.

The production of pilin monomers and assembly into protein nanowires can be scalable, simultaneously addressing the interrelated challenges of sustainable supply, engineering, and production of the electronics industry.

Embodiments described herein provide a method of synthesizing protein nanowires. In one embodiment, the method can comprise providing purified peptide building blocks. In one embodiment, the peptide building blocks are isolated from a recombinant host. The method can include suspending the purified peptide building blocks in an assembly buffer and forming an assembly composition by adding a hydrophobe to the assembly buffer to trigger self-assembly of the peptide building blocks. The method can include increasing molecular crowding by evaporation of a volume of the assembly buffer in the assembly composition to facilitate hydrophobe guided assembly to conductive nanowires.

In one embodiment, the method can further comprise conducting one or more elongation cycles to promote fiber formation, wherein the elongation cycle comprises providing additional peptide building blocks and/or hydrophobe into the assembly composition, mixing the assembly composition and evaporating the assembly buffer from the assembly composition.

In one embodiment, the method can comprise conducting about 4 cycles of elongation.

In one embodiment, the hydrophobe is octadecane.

In one embodiment, the hydrophobe is added to the assembly composition by loading the peptide building blocks into a column comprising particles and eluting the peptide building blocks into the assembly buffer, wherein the elution results in the elution of a portion of the particles of the column and the peptide building blocks into the assembly buffer and wherein the particles of the column are the hydrophobes in the assembly composition.

In one embodiment, the hydrophobe is C18-silica particles.

In one embodiment, the recombinant host is E.coli. In one embodiment, the peptide building blocks are modified PilA peptides. In one embodiment, the peptide building blocks are truncated pilin peptides from G. sulfurreducens. In one embodiment, the peptide building blocks are pilA$_{19}$ peptides from G. sulfurreducens. In one embodiment, the peptide building blocks are truncated PilA$_n$ peptides, wherein the truncated PilA$_n$ peptides have the amino acid sequences selected from the group consisting of SEQ ID NO:2, SEQ ID NO:3, SEQ ID NO:4, and SEQ ID NO:5.

In one embodiment, the nanowires formed have a length from about 0.5 μm to about 10 μm. In one embodiment, the nanowires formed have a length from about 2 μm to about 8 μm. In one embodiment, the nanowires formed have a length from about 4 μm to about 7 μm. In one embodiment, the nanowires formed have a length from about 5 μm to about 7 μm.

Embodiments described herein provide a method of synthesizing protein nanowires. In one embodiment, the method can comprise providing purified peptide building blocks, wherein the peptide building blocks are isolated from a recombinant host. The method can include suspending the purified peptide building blocks and a hydrophobe in an assembly buffer and forming an assembly composition by loading the peptide building blocks into a column comprising particles and co-eluting the peptide building blocks and a portion of the particles of the column into the assembly buffer and wherein the particles of the column are the hydrophobes in the assembly composition. The method can include increasing molecular crowding by evaporation of a volume of the assembly buffer in the assembly composition to facilitate hydrophobe guided assembly to conductive nanowires. In one embodiment, the hydrophobe is C18-silica particles Embodiments described herein provide a composition comprising protein nanowires wherein the nanowires comprise peptide building blocks derived from PilA peptides and the nanowires have a length of at least about 2 μM. In one embodiment, the nanowires have a length from about 2 μM to about 10 μM. In one embodiment, the nanowires have a length from about 5 μM to about 7 μM.

In one embodiment, the peptide building blocks are modified PilA peptides. In one embodiment, the peptide building blocks are truncated PilA peptides. In one embodiment, the peptide building blocks are PilA$_{19}$ peptides. In one embodiment, the nanowires have a length of at least about 2 μM. In one embodiment, the nanowires have a length from about 2 μM to about 10 μM. In one embodiment, the nanowires have a length of from about 5 μM to about 7 μM.

In one embodiment, the nanowires have an average diameter of about 2 nm.

In one embodiment, the nanowires have a Circular Dichroism (CD) profile with an intensity ratio of 220 nm/208 nm from about 0.7 and to about 0.9 or higher.

Embodiments described herein provide a device comprising synthesized protein nanowires wherein the nanowires comprise peptide building blocks derived from PilA peptides and the nanowires have a length of at least about 2 μM. In one embodiment, the nanowires have a length from about 2 μM to about 10 μM. In one embodiment, the nanowires have a length of from about 5 μM to about 7 μM.

The various embodiments described herein highlight the potential of improved methods functionalizing electrodes and incorporation of the improved electrodes in BESs. The improved electrodes allow various additional industrial needs to be met.

All ranges given are intended to further include "any range therebetween" whether or not this is affirmatively stated.

All publications, patents and patent documents are incorporated by reference herein, as though individually incorporated by reference, each in their entirety, as though individually incorporated by reference. In the case of any inconsistencies, the present disclosure, including any definitions therein, will prevail.

Although specific embodiments have been illustrated and described herein, it will be appreciated by those of ordinary skill in the art that any procedure that is calculated to achieve the same purpose may be substituted for the specific embodiments shown. This application is intended to cover any adaptations or variations of the present subject matter.

What is claimed is:

1. A method of synthesizing protein nanowires comprising:
   providing purified peptide building blocks;
   suspending the purified peptide building blocks in an assembly solvent;
   forming an assembly composition by addition of one or more hydrophobic molecules to the assembly solvent with the purified peptide building blocks to trigger self-assembly of the peptide building blocks; and
   increasing molecular crowding by evaporation of a volume of the assembly solvent in the assembly composition to facilitate hydrophobe guided assembly to conductive nanowires, and
   wherein the peptide building blocks are PilA19 peptides from *G. sulfurreducens;*
   wherein the one or more hydrophobic molecules comprise octadecane, C18-silica particles, or an alkane, or wherein the one or more hydrophobic molecules are a detergent, dextran, or methacrylate and are added directly to the assembly solvent or in surface constrained form as a coating on silica or agarose bead.

2. The method of claim 1 further comprising conducting one or more elongation cycles to promote fiber formation, wherein the elongation cycle comprises providing additional peptide building blocks and/or one or more hydrophobic molecules into the assembly composition, mixing the assembly composition and evaporating the assembly solvent from the assembly composition.

3. The method of claim 1 wherein about four elongation cycles are conducted.

4. The method of claim 1 wherein the one or more hydrophobic molecules is added to the assembly composition by loading the peptide building blocks into a column comprising particles and eluting the peptide building blocks into the assembly solvent, wherein the elution results in the elution of a portion of the particles of the column and the peptide building blocks into the assembly solvent and wherein the particles of the column are the one or more hydrophobic molecules in the assembly composition.

5. The method of claim 1 wherein the nanowires formed have a length from about 0.3 μm to about 10 μm.

* * * * *

SEQUENCE LISTING

```
Sequence total quantity: 15
SEQ ID NO: 1            moltype = AA  length = 61
FEATURE                 Location/Qualifiers
source                  1..61
                        mol_type = protein
                        organism = Geobacter sulfurreducens
SEQUENCE: 1
FTLIELLIVV AIIGILAAIA IPQFSAYRVK AYNSAASSDL RNLKTALESA FADDQTYPPE  60
S                                                                 61

SEQ ID NO: 2            moltype = AA  length = 51
FEATURE                 Location/Qualifiers
source                  1..51
                        mol_type = protein
                        organism = Geobacter sulfurreducens
SEQUENCE: 2
```

```
                             -continued

AIIGILAAIA IPQFSAYRVK AYNSAASSDL RNLKTALESA FADDQTYPPE S          51

SEQ ID NO: 3              moltype = AA   length = 42
FEATURE                   Location/Qualifiers
source                    1..42
                          mol_type = protein
                          organism = Geobacter sulfurreducens
SEQUENCE: 3
AIPQFSAYRV KAYNSAASSD LRNLKTALES AFADDQTYPP ES                    42

SEQ ID NO: 4              moltype = AA   length = 41
FEATURE                   Location/Qualifiers
source                    1..41
                          mol_type = protein
                          organism = Geobacter sulfurreducens
SEQUENCE: 4
IPQFSAYRVK AYNSAASSDL RNLKTALESA FADDQTYPPE S                     41

SEQ ID NO: 5              moltype = AA   length = 39
FEATURE                   Location/Qualifiers
source                    1..39
                          mol_type = protein
                          organism = Geobacter sulfurreducens
SEQUENCE: 5
QFSAYRVKAY NSAASSDLRN LKTALESAFA DDQTYPPES                        39

SEQ ID NO: 6              moltype = DNA   length = 38
FEATURE                   Location/Qualifiers
misc_feature              1..38
                          note = A synthetic primer
source                    1..38
                          mol_type = other DNA
                          organism = synthetic construct
SEQUENCE: 6
ggtggttgct cttccaactt caccottato gagctgct                         38

SEQ ID NO: 7              moltype = DNA   length = 36
FEATURE                   Location/Qualifiers
misc_feature              1..36
                          note = A synthetic primer
source                    1..36
                          mol_type = other DNA
                          organism = synthetic construct
SEQUENCE: 7
ggtggtctgc agtcattaac tttcgggcgg ataggt                           36

SEQ ID NO: 8              moltype = DNA   length = 36
FEATURE                   Location/Qualifiers
misc_feature              1..36
                          note = A synthetic primer
source                    1..36
                          mol_type = other DNA
                          organism = synthetic construct
SEQUENCE: 8
ggtggtctgc agtcattaac tttcgggcgg ataggt                           36

SEQ ID NO: 9              moltype = DNA   length = 38
FEATURE                   Location/Qualifiers
misc_feature              1..38
                          note = A synthetic primer
source                    1..38
                          mol_type = other DNA
                          organism = synthetic construct
SEQUENCE: 9
ggtggttgct cttccaacgc gatcatcggt attctcgc                         38

SEQ ID NO: 10             moltype = DNA   length = 38
FEATURE                   Location/Qualifiers
misc_feature              1..38
                          note = A synthetic primer
source                    1..38
                          mol_type = other DNA
                          organism = synthetic construct
SEQUENCE: 10
ggtggttgct cttccaacgc gattccgcag ttctcggc                         38

SEQ ID NO: 11             moltype = DNA   length = 36
FEATURE                   Location/Qualifiers
misc_feature              1..36
```

```
                        note = A synthetic primer
source                  1..36
                        mol_type = other DNA
                        organism = synthetic construct
SEQUENCE: 11
ggtggtctgc agtcattaac tttcgggcgg ataggt                          36

SEQ ID NO: 12           moltype = DNA  length = 38
FEATURE                 Location/Qualifiers
misc_feature            1..38
                        note = A synthetic primer
source                  1..38
                        mol_type = other DNA
                        organism = synthetic construct
SEQUENCE: 12
ggtggttgct cttccaacat tccgcagttc tcggcgta                        38

SEQ ID NO: 13           moltype = DNA  length = 36
FEATURE                 Location/Qualifiers
misc_feature            1..36
                        note = A synthetic primer
source                  1..36
                        mol_type = other DNA
                        organism = synthetic construct
SEQUENCE: 13
ggtggtctgc agtcattaac tttcgggcgg ataggt                          36

SEQ ID NO: 14           moltype = DNA  length = 38
FEATURE                 Location/Qualifiers
misc_feature            1..38
                        note = A synthetic primer
source                  1..38
                        mol_type = other DNA
                        organism = synthetic construct
SEQUENCE: 14
ggtggttgct cttccaacca gttctcggcg tatcgtgt                        38

SEQ ID NO: 15           moltype = DNA  length = 36
FEATURE                 Location/Qualifiers
misc_feature            1..36
                        note = A synthetic primer
source                  1..36
                        mol_type = other DNA
                        organism = synthetic construct
SEQUENCE: 15
ggtggtctgc agtcattaac tttcgggcgg ataggt                          36
```